(12) United States Patent
Erstad et al.

(10) Patent No.: US 11,666,532 B2
(45) Date of Patent: Jun. 6, 2023

(54) TRANEXAMIC ACID ORAL SOLUTION

(71) Applicant: Hyloris Developments SA, Liège (BE)

(72) Inventors: Mary Beth G. Erstad, Plymouth, MN (US); Thomas Gerner Jacobsen, Leuven (BE); Mohammad Alkhalili, North Richland Hills, TX (US); L. Diane Bruce, Ft. Worth, TX (US); Paul Hafey, Keller, TX (US)

(73) Assignee: Hyloris Developments SA, Liege (BE)

( * ) Notice: Subject to any disclaimer, the term of this patent is extended or adjusted under 35 U.S.C. 154(b) by 0 days.

(21) Appl. No.: 16/243,234

(22) Filed: Jan. 9, 2019

(65) Prior Publication Data

US 2019/0224121 A1 Jul. 25, 2019

Related U.S. Application Data

(60) Provisional application No. 62/619,634, filed on Jan. 19, 2018.

(51) Int. Cl.
*A61K 9/08* (2006.01)
*A61K 31/195* (2006.01)
(Continued)

(52) U.S. Cl.
CPC .............. *A61K 9/08* (2013.01); *A61K 9/0053* (2013.01); *A61K 9/0063* (2013.01);
(Continued)

(58) Field of Classification Search
CPC ........................................................ A61P 7/04
See application file for complete search history.

(56) References Cited

U.S. PATENT DOCUMENTS 2,695,605 A * 11/1954 Gibbon ................... B25J 21/02
600/22
4,171,377 A 10/1979 Green et al.
(Continued)

FOREIGN PATENT DOCUMENTS

CN 101766551 B 5/2012
CN 103099800 A 5/2013
(Continued)

OTHER PUBLICATIONS

Hewson et al., Dental surgery with minimal factor support in the inhereited bleeding disorder population at the Alfred Hospital, Haemophilia (2011), vol. 17, 4pgs.
(Continued)

*Primary Examiner* — Savitha M Rao
*Assistant Examiner* — Andrew P Lee
(74) *Attorney, Agent, or Firm* — Neal, Gerber & Eisenberg LLP

(57) ABSTRACT

Methods and compositions are provided for treating a patient having a bleeding disorder during or after a dental procedure to reduce bleeding or need for factor replacement therapy. Aqueous pharmaceutical compositions are provided comprising tranexamic acid, sodium carboxymethyl cellulose, Tween® 20, and menthol wherein the composition exhibits good long term stability, little to no discoloration over time, and reduced bitterness compared to a control solution of tranexamic acid and water.

12 Claims, 1 Drawing Sheet

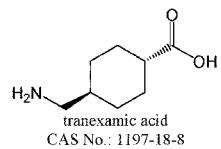

tranexamic acid
CAS No.: 1197-18-8

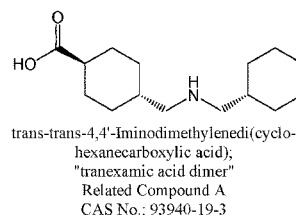

trans-trans-4,4'-Iminodimethylenedi(cyclo-
hexanecarboxylic acid);
"tranexamic acid dimer"
Related Compound A
CAS No.: 93940-19-3

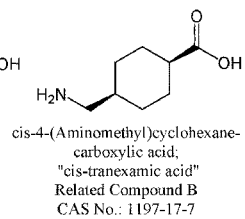

cis-4-(Aminomethyl)cyclohexane-
carboxylic acid;
"cis-tranexamic acid"
Related Compound B
CAS No.: 1197-17-7

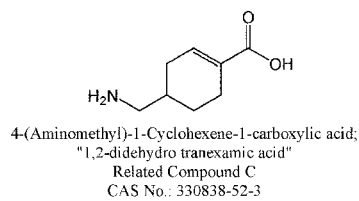

4-(Aminomethyl)-1-Cyclohexene-1-carboxylic acid;
"1,2-didehydro tranexamic acid"
Related Compound C
CAS No.: 330838-52-3

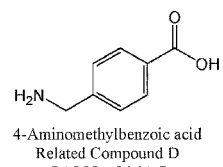

4-Aminomethylbenzoic acid
Related Compound D
CAS No.:56-91-7

(51) Int. Cl.
*A61K 47/10* (2017.01)
*A61K 47/14* (2017.01)
*A61K 47/26* (2006.01)
*A61K 47/38* (2006.01)
*A61K 9/00* (2006.01)
*A61P 7/04* (2006.01)

(52) U.S. Cl.
CPC ............ *A61K 31/195* (2013.01); *A61K 47/10* (2013.01); *A61K 47/14* (2013.01); *A61K 47/26* (2013.01); *A61K 47/38* (2013.01); *A61P 7/04* (2018.01)

(56) References Cited

U.S. PATENT DOCUMENTS

| | | | |
|---|---|---|---|
| 4,272,512 A | 6/1981 | Gaffar | |
| 4,272,513 A | 6/1981 | Gaffar | |
| 4,309,410 A | 1/1982 | Gaffar | |
| 4,465,662 A | 8/1984 | Sato et al. | |
| 4,649,044 A * | 3/1987 | Gomi | A61K 8/33 424/48 |
| 5,747,030 A * | 5/1998 | Kohnert | A61K 9/0019 424/94.64 |
| 5,817,297 A | 10/1998 | Ha et al. | |
| 6,811,769 B2 | 11/2004 | Watanabe | |
| 6,939,559 B1 | 9/2005 | Nishibe et al. | |
| 7,235,247 B2 | 6/2007 | Nishibe et al. | |
| 7,947,739 B2 | 5/2011 | Moore et al. | |
| 8,022,106 B2 | 9/2011 | Moore et al. | |
| 8,273,795 B2 | 9/2012 | Moore et al. | |
| 8,487,005 B2 | 7/2013 | Moore et al. | |
| 8,673,271 B2 | 3/2014 | Kato et al. | |
| 8,791,160 B2 | 7/2014 | Moore et al. | |
| 8,809,394 B2 | 8/2014 | Moore et al. | |
| 8,957,113 B2 | 2/2015 | Moore et al. | |
| 9,060,939 B2 | 6/2015 | Moore et al. | |
| 9,295,627 B2 | 3/2016 | Kohno et al. | |
| 9,301,936 B2 | 4/2016 | Buderer et al. | |
| 9,314,442 B2 | 4/2016 | Hallam et al. | |
| 9,387,178 B2 | 7/2016 | Joshi et al. | |
| 9,504,736 B2 | 11/2016 | Schmid-Schonbein et al. | |
| 9,775,821 B2 | 10/2017 | Hallam et al. | |
| 2003/0069213 A1 | 4/2003 | Ii et al. | |
| 2012/0022160 A1 | 1/2012 | Suzuki et al. | |
| 2012/0164357 A1 | 6/2012 | Suzuki et al. | |
| 2012/0302640 A1 | 11/2012 | Macalister | |
| 2016/0058723 A1 | 3/2016 | Lee et al. | |
| 2016/0206580 A1 | 7/2016 | Los et al. | |
| 2016/0263064 A1 | 9/2016 | Hallam et al. | |
| 2016/0287541 A1 | 10/2016 | Joshi et al. | |
| 2016/0325011 A1 | 11/2016 | Iwama et al. | |
| 2018/0000765 A1 | 1/2018 | Hallam et al. | |
| 2018/0214440 A1* | 8/2018 | Coates | A61Q 11/00 |

FOREIGN PATENT DOCUMENTS

| | | |
|---|---|---|
| CN | 105497052 A | 4/2016 |
| CN | 105963190 A | 9/2016 |
| EP | 2 695 605 A1 | 12/2014 |
| JP | 11228370 A | 8/1999 |
| JP | 2002068971 A | 3/2002 |
| JP | 2003063938 A | 3/2003 |
| JP | 2013121955 A | 6/2013 |
| JP | 5249558 B2 | 7/2013 |
| WO | 0037071 | 6/2000 |
| WO | 2007069429 A1 | 6/2007 |
| WO | 2013180019 A1 | 12/2013 |
| WO | 2016002787 A1 | 7/2016 |
| WO | 2016133483 A1 | 8/2016 |

OTHER PUBLICATIONS

Mancuso et al., Dental surgery in inherited bleeding disorders with minimal factor support: commentary, Haemophilia (2011), vol. 17, 2pgs.

Patatanian et al., Hemostatic Mouthwashes in Anticoagulated Patients Undergoing Dental Extraction, The Annuals of Pharmacotherapy, Dec. 2006, vol. 40, 6pgs.

Tengborn, Fibrinolytic Inhibitors in the Management of Bleeding Disorders, Treatment of Hemophilia, Nov. 2012, No. 42, 6pgs.

Van Galen et al., Antifibrinolytic therapy for preventing oral bleeding in patients with haemophilia or Von Willebrand disease undergoing minor oral surgery or dental extractions, Cochrane Database of Systematic Reviews, 2015, Issue 12, 35 pgs.

Lee et al., Effectiveness in controlling haemorrhage after dental scaling in people with haemophilia by using tranexamic acid mouthwash, British Dental Journal, Jan. 8, 2005, vol. 198, No. 1, 6pgs.

Nuvuula, et al., Efficacy of tranexamic acid mouthwash as an alternative for factor replacement in gingival bleeding during dental scaling in cases of hemophilia: A randomized clinical trial, Contemporary Clinical Dentistry, Jan.-Mar. 2014, vol. 5, Issue 1, 6pgs.

Hamid, et al., The Effect of Tranexamic Acid (Cyclokapron) on Post-Surgical Bleeding Following the Removal of Impacted Lower Wisdom Teeth in Healthy Individuals, Al-Rafidain Dent J, 2008, vol. 8, No. 2, 6pgs.

Tavenner, Use of Tranexamic Acid in Control of Haemorrhage after Extraction of Teeth in Haemophilia and Christmas Disease, British Medical Journal, 1972, vol. 2, 2pgs.

Forbes, et al., Tranexamic Acid in Control of Haemorrhage after Dental Extraction in Haemophilia and Christmas Disease, British Medical Journal, May 6, 1972, vol. 2., 3pgs.

Gringeri et al., Cost of care and quality of life of patients with hemophilia complicated by inhibitors: the COCIS Study Group, Blood, Oct. 1, 2003, vol. 102, No. 7, 6pgs.

Walsh et al., Impact of inhibitors on hemophilia A mortality in the United States, American Journal of Hematology, May 2015, vol. 90, No. 5, 6pgs.

Franchini et al., Dental procedures in adult patients with hereditary bleeding disorders: 10 years experience in three Italian Hemophilia Centers, Haemophilia 2005, vol. 11, 6 pgs.

Gouveia et al., Phosphoric acid rate addition effect in the hydroxyapatite synthesis by neutralization method, Materials Science Forum vols. 530-531, pp. 593-598 (2006), 7pgs.

Phosphate Buffers, https://www.chem.fsu.edu/chemlab/Mastering/PhosphateBuffers.htm, 2pgs.

* cited by examiner

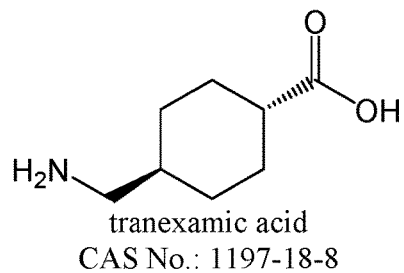

tranexamic acid
CAS No.: 1197-18-8

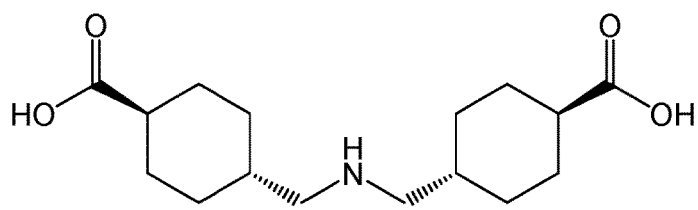

trans-trans-4,4'-Iminodimethylenedi(cyclo-
hexanecarboxylic acid);
"tranexamic acid dimer"
Related Compound A
CAS No.: 93940-19-3

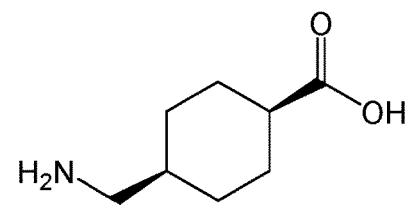

cis-4-(Aminomethyl)cyclohexane-
carboxylic acid;
"cis-tranexamic acid"
Related Compound B
CAS No.: 1197-17-7

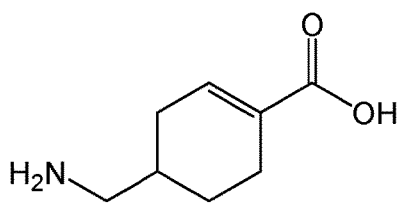

4-(Aminomethyl)-1-Cyclohexene-1-carboxylic acid;
"1,2-didehydro tranexamic acid"
Related Compound C
CAS No.: 330838-52-3

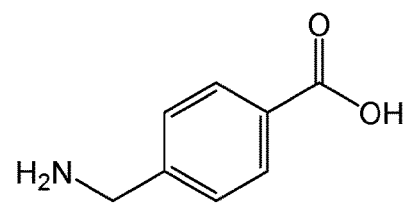

4-Aminomethylbenzoic acid
Related Compound D
CAS No.:56-91-7

TRANEXAMIC ACID ORAL SOLUTION

CROSS-REFERENCE TO RELATED APPLICATIONS

This application claims the benefit of U.S. Provisional Patent Application No. 62/619,634, which was filed on Jan. 19, 2018, the disclosure of which is incorporated by reference in its entirety herein.

BACKGROUND

Tranexamic acid is an antifibrinolytic agent that competitively inhibits the activation of plasminogen to plasmin, an enzyme that degrades fibrin clots, fibrinogen, and other plasma proteins, including the pro-coagulant factors V and VIII.

Tranexamic acid has a long history of clinical use as an anti-fibrinolytic drug. Approved uses include a range of indications: short-term use for prevention or treatment of hemorrhage under conditions of general or local fibrinolysis, which includes for instance pre-/postoperative hemorrhage, heavy menstrual bleeding and hereditary angioneurotic edema.

Commercial compositions including CYKLOKAPRON (tranexamic acid) injection and oral tablets were approved for use in the United States in 1986. CYKLOKAPRON injection is used for dental extraction in patients with hemophilia. CYKLOKAPRON tablets are used to prevent excess bleeding in patients with menorrhagia (heavy menstrual bleeding). More recently, LYSTEDA (Tranexamic Acid) tablets were approved for use in the treatment of heavy menstrual bleeding. However, in order to limit systemic exposure to tranexamic acid, alternative topical formulations are desirable.

Tranexamic acid oral rinse compositions are known. Prior art compositions are not stable for long term shelf storage and are subject to discoloration. Additionally, bitterness of prior art oral rinse solutions of tranexamic acid has limited their use.

U.S. Pat. No. 4,465,662, Sato et al., discloses oral compositions comprising tranexamic acid and carvone that exhibit reduced bitterness. Toothpaste formulations comprising specific ratios of sorbitol to glycerol are disclosed for prevention of discoloration. However, as provided herein, it has been discovered that solution formulations containing tranexamic acid and sorbitol and/or glycerin exhibit discoloration upon storage.

EP 2695605 discloses liquid compositions comprising tranexamic acid in (tris(hydroxymethyl)aminomethane) (TRIS) or glycine buffer systems as exhibiting decreased discoloration compared to phosphate or isoleucine buffer systems in accelerated stability tests. TRIS or glycine buffering agents were said to maintain pH 6 to 8 to avoid discoloration. However, TRIS or glycine buffers may not be optimal for a target pH range of about pH 5 to 6 for use in formulation development.

Clinical studies have demonstrated that the use of local tranexamic acid, as a supplement to the currently used systemic therapy, significantly reduces the incidence of bleeding during or after dental procedures. For example, A. H. P. Lee et al. in 2005, *British Dental journal*, Vol. 198: pp. 33-38, showed effectiveness in controlling hemorrhage after dental scaling in people with haemophilia by using tranexamic acid mouthwash. Sivakumar Nuvvula et al., 2014, *Contemp Clin Dent*, Vol. 5(1): 49-53, demonstrated use of tranexamic acid mouthwash as an alternative for factor replacement in gingival bleeding during dental scaling in cases of hemophilia.

Therefore, further improved tranexamic acid oral rinse compositions exhibiting improved stability and taste characteristics are desirable.

SUMMARY

Some embodiments of the invention provide an aqueous pharmaceutical composition for topical administration of tranexamic acid in the oral cavity. With respect to these embodiments, the composition includes water, a non-ionic surfactant, a preservative, a viscosity enhancer, a thickening agent, a pH adjuster, a sweetener, and a flavoring agent. The composition preferably includes greater than 40% water.

Other embodiments of the invention are directed to an aqueous pharmaceutical composition that includes about 3% wt/vol to about 7% wt/vol tranexamic acid, greater than 40% water, a surfactant, a thickening agent, a viscosity enhancer, and a flavoring agent. With respect to these embodiments, the composition retains at least about 90% of the tranexamic acid in solution in undegraded form after storage for at least 6 months at about 25° C. and about 40% relative humidity.

In other embodiments, the invention provides a method for reducing or preventing hemorrhage in a patient having a bleeding disorder during or following a dental procedure. The method includes administering an aqueous pharmaceutical composition comprising tranexamic acid, water, a non-ionic surfactant, a preservative, a viscosity enhancer, a thickening agent, a pH adjuster, a sweetener, and a flavoring agent.

Still other embodiments are directed to a method for reducing or preventing hemorrhage in a patient on anticoagulant, fibrinolytic or thrombolytic therapy during or following a dental procedure. The method includes administering an aqueous pharmaceutical composition comprising tranexamic acid, water, a non-ionic surfactant, a preservative, a viscosity enhancer, a thickening agent, a pH adjuster, a sweetener, and a flavoring agent.

BRIEF DESCRIPTION OF THE DRAWINGS

FIG. 1 shows chemical structures of tranexamic acid and degradant tranexamic acid related compounds A, B, C and D.

DETAILED DESCRIPTION

Definitions

The singular forms "a", "an" and "the" are intended to include the plural forms as well, unless the context clearly indicates otherwise.

The term "and/or" refers to and encompasses any and all possible combinations of one or more of the associated listed items.

The term "about," as used herein when referring to a measurable value such as an amount of a compound, dose, time, temperature, and the like, is meant to encompass variations within the error of measurement for the specified amount.

Unless otherwise specified, all percentage "%" values are expressed as weight percent compared to total weight of the composition.

The term "therapeutically effective amount" refers to the amount of a compound that, when administered to a subject for treating a disease or condition, is sufficient to effect such treatment to fully or substantially alleviate the symptoms of the disease state or condition. The "therapeutically effective amount" can vary depending on the compound, the disease and its severity, and the condition, age, weight, gender etc. of the subject to be treated. In some embodiments, the effective amount of tranexamic acid is the amount sufficient to prevent or alleviate hemorrhage during and following dental procedures. In some embodiments, the effective amount of tranexamic acid is an amount sufficient to avoid reducing, interrupting or discontinuing anticoagulant, fibrinolytic or thrombolytic therapy in a patient in need thereof during and following dental procedures. In some embodiments, the effective amount of tranexamic acid is an amount sufficient to reduce the need for factor replacement therapy in the patient during and following dental procedures. In some embodiments, the effective amount of tranexamic acid is an amount sufficient to reduce the need for antifibrinolytic therapy in the patient during and following dental procedures.

The terms "treating" and "treatment" of a disease state or condition include: (i) preventing the disease state or condition, i.e., causing the clinical symptoms of the disease state or condition not to develop in a subject that may be exposed to or predisposed to the disease state or condition, but does not yet experience or display symptoms of the disease state or condition, (ii) inhibiting the disease state or condition, i.e., arresting the development of the disease state or condition or its clinical symptoms, or (iii) relieving the disease state or condition, i.e., causing temporary or permanent regression of the disease state or condition or its clinical symptoms. In some embodiments, the terms "treating" or "treatment" refer to prevention or alleviation of hemorrhage during and following dental procedures.

The term "solution" refers to a clear, homogeneous liquid dosage form that contains at least one active pharmaceutical chemical substance dissolved in a solvent or mixture of mutually miscible solvents.

The term "topical administration in the oral cavity" refers to administration to the skin or mucosa of the mouth. For example, this would include a swish and spit administration of a tranexamic acid mouth rinse solution. Administration to the oral mucosa may be performed by swishing the tranexamic acid solution inside the mouth of the patient for a period of time then spitting it out. In some embodiments, the tranexamic acid oral rinse solution is swished or held in the mouth of the patient for at least 30 seconds, at least 45 seconds, at least 60 seconds, at least 75 seconds, at least 90 seconds, or at least 120 seconds before spitting it out. In some aspects, topical administration in the oral cavity includes periodontal administration. The tranexamic acid oral rinse composition as provided herein may be administered topically in the oral cavity in the form of a solution. For example, the tranexamic acid oral rinse composition may be administered immediately after a dental procedure in patients with hemophilia, comprising administering 10 ml of a 5% solution as an oral rinse for two minutes. The administration of the oral rinse may be continued three or four times daily for up to eight (8) days.

Tranexamic Acid

Tranexamic acid, also known as trans-4-(aminomethyl) cyclohexanecarboxylic acid, also referred to as TXA, for example having CAS RN: 1197-18-8, is an active pharmaceutical ingredient (API) that is a competitive inhibitor of plasminogen activation

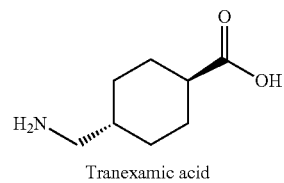 [SMILES: NC[C@H]1CC[C@H](C(=O)O)CC1]

Tranexamic acid

Tranexamic acid is an antifibrinolytic hemostatic agent used to prevent or treat severe hemorrhage. Available literature demonstrates the effectiveness of local antifibrinolytic therapy for patients with inherited bleeding disorders for dental procedures.

Tranexamic acid may be administered intravenously, orally and as a mouth rinse. Historically, tranexamic acid concentrations up to 10 mg per mL blood have no influence on the platelet count, the coagulation time, or various coagulation factors in whole blood or citrated blood from normal subjects. On the other hand, tranexamic acid in concentrations of 1 mg to 10 mg per mL blood prolongs the thrombin time. After intravenous dose of 1 g, the plasma concentration time curve shows a tri-exponential decay with a half-life of about 2 hours for the terminal elimination phase. The initial volume of distribution is about 9 to 12 liters. The plasma protein binding of tranexamic acid is about 3% at therapeutic plasma levels and seems to be fully accounted for by its binding to plasminogen (does not bind serum albumin). Only a small fraction of the drug is metabolized (less than 5%). Urinary excretion is the main route of elimination via glomerular filtration. Overall renal clearance is equal to overall plasma clearance (100 to 116 mL/min), and more than 95% of the dose is excreted in the urine as unchanged drug. Excretion of tranexamic acid is about 90% at 24 hours after intravenous administration of 10 mg per kg body weight.

Absorption of tranexamic acid after oral administration in humans represents approximately 30 to 50% of the ingested dose and bioavailability is not affected by foodintake.

Systemically, tranexamic acid binds considerably more strongly than epsilon aminocaproic acid (EACA) to both the strong and weak sites in the plasminogen molecule in a ratio corresponding to the difference in potency between the compounds. The pharmacological significance of the binding to these different sites has not yet been evaluated. Tranexamic acid does not bind to serum albumin. The plasma protein binding seems to be fully accounted for by its binding to plasminogen and appears to be negligible at therapeutic plasma levels of 5-10 mg/L.

Possible routes of biotransformation are acetylation or deamination followed by oxidation or reduction. After oral administration approximately 50% of the parent compound, 2% of the deaminated dicarboxylic acid, and 0.5% of the acetylated product are excreted. Tranexamic acid is eliminated by glomerular filtration, excretion being about 30% at one hour, 55% at three hours and 90% at 24 hours after intravenous administration of 10 mg per kg body weight. After oral administration of 10-15 mg per kg body weight, excretion was 1% at one hour, 7% at three hours and 39% at 24 hours.

Intravenous administration of 10 mg per kg body weight gave plasma concentrations of 18.3 μg, 9.6 μg and 5 μg per mL one, three and five hours after the injection. When administered 36-48 hours before surgery in four doses of 10-20 mg per kg body weight, an antifibrinolytically active concentration (10 µg/mL) of tranexamic acid remained up to 17 hours in the tissues investigated, and up to 7-8 hours in the serum.

Tranexamic acid crosses the placenta. After an intravenous injection of 10 mg per kg body weight the concentration can rise to about 30 µg per mL of fetal serum. Tranexamic acid also passes over into the breast milk during lactation in concentrations 1/100 of the corresponding serum levels. After both oral and intravenous administration tranexamic acid passes into the semen and inhibits its fibrinolytic activity, but without affecting the motility of the spermatozoa. The ability of tranexamic acid to cross the blood-brain barrier has been demonstrated when administered to patients with ruptured intracranial aneurysms. Tranexamic acid diffuses rapidly to the joint fluid and to the synovial membrane. In the joint fluid the same concentration was obtained as in the serum. The biological half-life in the joint fluid was about 3 hours.

Three hours after a single oral dose of 25 mg per kg body weight, the peak serum level was 15.4 mg per L and the aqueous humor level was 1.6 mg per L.

Pharmacokinetic studies have compared the distribution of tranexamic acid in plasma and saliva after mouth rinsing and oral administration. After oral administration, the mean plasma concentration of tranexamic acid reached its maximum after 120 minutes at approximatively 7 µg per mL, whereas the saliva levels of tranexamic acid were undetectable at any time points. After mouth rinse, the plasma concentrations remained below 2 µg per mL, whereas the concentrations found in saliva were initially above 200 µg per mL and remained above therapeutic levels for more than 2 hours. These findings indicate that fibrinolysis in the oral cavity can be inhibited by local administration of tranexamic acid.

An oral rinse dosage form of tranexamic acid for topical administration will facilitate the use of antifibrinolytic therapy in dental patients and minimize systemic exposure from administration of the injection dosage form.

Excipients

Sodium carboxymethyl cellulose is also known as carboxymethyl cellulose sodium or carboxymethyl cellulose, sodium salt, and acronyms Na CMC, or sodium CMC, for example, having Chemical Abstracts Service Registry Number (CAS RN): 9004-32-4, is non-foaming, hydrophilic water soluble polymer that may be used as a thickening agent.

Poloxamer 407 is a non-ionic surfactant also known as Poly(ethylene glycol)-block-poly(propylene glycol)-block-poly(ethylene glycol), an A-B-A block copolymer having CAS Reg No.: 9003-11-6. Poloxamer 407 has an HLB (hydrophilic-lipophilic balance) value of 18-23.

Tween 20 is a non-ionic surfactant also known as polysorbate 20, refers to polyoxyethylene sorbitan monolaurate, or polyethylene glycol sorbitan monolaurate, for example having CAS RN: 9005-64-5, having M.W. 1227.54 g/mol.

Tween 80 is a non-ionic surfactant also known as polyoxyethylene (20)sorbitan monooleate, for example having CAS RN: 9005-65-6, having M.W. 604.816 g/mol.

Sucrose stearate, also known as sucrose monostearate, or alpha-D-Glucopyranoside, beta-D-fructofuranosyl, monooctadecanoate, for example having CAS RN: 25168-73-4, is a type of non-ionic sucrose ester surfactant.

Sucrose laurate, also known as sucrose monolaurate, or beta-D-Fructofuranosyl-alpha-D-glucopyranoside, monododecanoate, for example having CAS RN: 25339-99-5, is a type of non-ionic sucrose ester surfactant.

Compositions

Pharmaceutical compositions in the form of aqueous oral rinse formulations comprising tranexamic acid are described. In some embodiments, an aqueous oral rinse formulation is provided comprising from about 3% wt/vol to about 7% wt/vol, about 4% wt/vol to about 6% wt/vol, or about 5% wt/vol tranexamic acid. In some embodiments, an aqueous oral rinse formulation is provided comprising from about 30 to about 70 mg/mL, about 40 to about 60 mg/mL, about 45 mg/mL to about 55 mg/mL, or about 50 mg/mL tranexamic acid.

In some embodiments, pharmaceutical compositions are provided in the form of aqueous oral rinse formulations comprising tranexamic acid in an amount effective to reduce the need for factor replacement therapy (FRT) in the patient. FRT is a main method for reducing hemorrhage in people with bleeding disorders such as hemophilia A and hemophilia B. However, FRT is expensive, and its use both as plasma and recombinant factor therapy runs the risk of formation of inhibitors. In addition, there is a possibility of transmission of blood borne viruses including HIV, hepatitis A, B, C, G and parvovirus with HRT. In certain aspects the amount effective to reduce the need for factor replacement therapy is about 10 mL of a 5% oral rinse solution of tranexamic acid, or the equivalent, held in the mouth for 2 minutes. In some embodiments, the effective amount to reduce the need for factor replacement therapy is about 5 mL of a 10% oral rinse solution of tranexamic acid, or an equivalent, held in the mouth for about 2 minutes. In some embodiments, an effective amount of tranexamic acid in an oral rinse solution is a concentration of from about 3% wt/vol to about 12% wt/vol, about 3% wt/vol to about 7% wt/vol, about 4% wt/vol to about 6% wt/vol, or about 5% wt/vol tranexamic acid.

In some embodiments, pharmaceutical compositions are provided in the form of aqueous oral rinse formulations comprising tranexamic acid in an amount effective to prevent or reduce hemorrhage in a patient following a dental procedure such as scaling or tooth extraction. In one embodiment, a mouth rinse composition having a concentration of about 4-6% wt/vol tranexamic acid is employed in an amount of about 10 mL, for example when used for about 2 minutes, about 4 times daily for 2 to 7 days post operatively to reduce the need for intravenous antifibrinolytic therapy. (Hamid et al., 2008).

In some embodiments, aqueous oral rinse tranexamic acid solution formulations are provided having greater than 40%, greater than 45%, or greater than 50% by volume water. In some embodiments, any water suitable for pharmaceutical purposes may be employed. The water is selected from purified water or water for injection as defined by U.S. Pharmacopeia. In a specific embodiment, purified water USP is used.

In some embodiments, an aqueous formulation of tranexamic acid is provided wherein all components remain in solution, and exhibit little to no discoloration over storage conditions for at least 3 months, at least 6 months, at least 9 months, at least 12 months, at least 18 months, at least 24 months, at least 30 months, at least 36 months, or at least 48 months under storage at standard room temperature and humidity conditions, such as 25° C. and 40% relative humidity. In a particular aspect, stable aqueous tranexamic acid formulations are provided, exhibiting minimal discoloration as determined by a $\Delta E^*$ value of <3, <4, <5, or <7 in a colorimetric assay when stored at 25° C. at 40% RH after a period of 3 months, 6 months, 9 months, or 12 months. In another particular aspect, stable aqueous tranexamic acid formulations are provided, exhibiting a $\Delta E^*$ value of <4, <5, or <7 in a colorimetric assay when stored at 40° C. at 25% RH after a period of 3 months, 6 months, 9 months, or 12 months. In some embodiments, the colorimetric assay employs the formula: $\Delta E^*=[\Delta L^{*2}+\Delta a^{*2}+\Delta b^{*2}]^{1/2}$, using L* a* b* coordinates, as defined herein. In some embodiments, formulations are stored in the dark.

In some embodiments, the tranexamic acid compositions provided herein may be stored in glass, HDPE (high density polyethylene), or PET (polyethylene terephthalate) bottles.

In some embodiments, the compositions provided herein capable of maintaining at least about 90%, 95%, 97.5%, 98%, 99%, 99.5%, or 99.7% of the release, or "as manufactured," amount of tranexamic acid in undegraded form after storage for at least 6 months at 25° C. at 40% relative humidity when measured by liquid chromatography. In some embodiments, the compositions provided herein capable of maintaining at least about 90%, 95%, 97.5%, 98%, 99%, or 99.5% of the release, or "as manufactured," amount of tranexamic acid in undegraded form after storage for at least 12 months at 25° C. at 40% relative humidity when measured by liquid chromatography. In some embodiments, the compositions provided herein capable of maintaining at least about 90%, 95%, 97.5%, 98%, 99%, 99.5% of the release, or "as manufactured," amount of tranexamic acid in undegraded form after storage for at least 18 months at 25° C. at 40% relative humidity when measured by liquid chromatography. In some embodiments, the compositions provided herein capable of maintaining at least about 90%, 95%, 97.5%, 98%, 99% of the release, or "as manufactured," amount of tranexamic acid in undegraded form after storage for at least 24 months at 25° C. at 40% relative humidity when measured by liquid chromatography. In some embodiments, the compositions provided herein capable of maintaining at least about 90%, 95%, 97.5%, 98%, 99% of the release, or "as manufactured," amount of tranexamic acid in undegraded form after storage for at least 36 months at 25° C. at 40% relative humidity when measured by liquid chromatography. In some embodiments, the compositions provided herein capable of maintaining at least about 90%, 95%, 97.5%, 98% of the release, or "as manufactured," amount of tranexamic acid in undegraded form after storage for at least 48 months at 25° C. at 40% relative humidity when measured by liquid chromatography.

In some embodiments, the compositions provided herein capable of maintaining at least about 90%, 95%, 97.5%, 98%, 99%, 99.5%, or 99.7% of the release, or "as manufactured," amount of tranexamic acid in undegraded form after storage for at least 6 months at 40° C. at 25% relative humidity when measured by liquid chromatography. In some embodiments, the compositions provided herein capable of maintaining at least about 90%, 95%, 97.5%, 98%, 99%, 99.5%, 99.7%, or 99.8% of the release, or "as manufactured," amount of tranexamic acid in undegraded form after storage for at least 12 months at 40° C. at 25% relative humidity when measured by liquid chromatography. In some embodiments, the compositions provided herein capable of maintaining at least about 90%, 95%, 97.5%, 98%, 99%, 99.5%, 99.7%, or 99.8% of the release, or "as manufactured," amount of tranexamic acid in undegraded form after storage for at least 18 months at 40° C. at 25% relative humidity when measured by liquid chromatography.

In some embodiments, a solution composition comprising tranexamic acid, sodium carboxymethyl cellulose, propylene glycol and menthol exhibits reduced bitterness, improved overall taste, and/or improved mouth feel compared to a solution of tranexamic acid alone, and exhibits good storage stability without phase separation.

pH Adjuster

Tranexamic acid in aqueous solution without a pH adjuster may range from pH 6.5 to 8.0. Therefore, in some embodiments, a pH adjuster is employed in the tranexamic aqueous formulations to adjust the pH to 4.5 to 6.5, preferably pH 5.0 to 6.0, or about pH 5.5. In some embodiments, the pH adjuster is any pharmaceutically acceptable pH adjuster known in the art. In some embodiments, the pH adjuster is selected from phosphoric acid, hydrochloric acid, nitric acid, sulfuric acid, hydrobromic acid, citric acid, malic acid, adipic acid, ascorbic acid, tartaric acid, lactic acid, and combinations thereof. In some embodiments, the pH adjuster is phosphoric acid. The pH adjuster may be employed in the composition in an amount in the range of about 0.1 wt % to 1 wt %, or about 0.2 to 0.5 wt %, or about 0.3 to 0.4 wt % to adjust the pH range as specified.

Surfactant

In some embodiments, an aqueous formulation of tranexamic acid is provided that is a solution formulation comprising a surfactant. The surfactant may serve as an emulsifier or dispersing agent to enhance homogeneity of the solution composition. In some embodiments, the surfactant is selected from a non-ionic surfactant that helps avoid phase separation of the composition. In some embodiments the surfactant is selected from any pharmaceutically acceptable non-ionic surfactant known in the art. In some embodiments, the composition does not include an anionic surfactant.

In some embodiments, the surfactant is a non-ionic surfactant selected from polyoxyethylene sorbitan monolaurate (e.g., Tween® 20), polyoxyethylene (20)sorbitan monooleate (e.g., Tween® 80), Poly(ethylene glycol)-block-poly(propylene glycol)-block-poly(ethylene glycol) (e.g., Poloxamer® 407), Sucrose Stearate, and Sucrose Laurate. In a specific embodiment, the surfactant is Tween 20. The surfactant is used in the aqueous tranexamic acid formulation in an amount from 0.1 to 2 wt %, or 0.5 to 1 wt % based on the weight of the composition.

Thickening Agent

In some embodiments, an aqueous formulation of tranexamic acid is provided that is a solution formulation comprising a thickening agent that is a hydrophilic water solublepolymer. In some embodiments, the thickening agent is a water soluble pharmaceutically acceptable polymer. In some embodiments, the thickening agent is not a superabsorbent polymer such as sodium polyacrylate. In some embodiments, the thickening agent may be selected from xanthan gum, sodium alginate, sodium carboxymethyl cellulose or starch. In some embodiments, the thickening agent is a water soluble, non-foaming pharmaceutically acceptable polymer. Foam testing may be performed by vigorously shaking a 0.1% solution of the thickening agent in water. If the thickening agent is non-foaming, no layer of foam appears. This test distinguishes, e.g., sodium carboxymethyl cellulose from other cellulose ethers and alginates and natural gums. In some embodiments, the thickening agent is sodium carboxymethyl cellulose. In some embodiments, the thickening agent is present in the aqueous tranexamic acid solution composition at from 0.05 wt % to 1 wt %, 0.1 wt % to 0.5 wt %, or 0.2 wt % to 0.3 wt %. The thickening agent aids in improving mouthfeel of the composition, and helps to alleviate the bitter taste of the composition when combined with the flavoring.

In some embodiments, compositions are provided comprising tranexamic acid, water, a thickening agent and a surfactant, wherein the compositions exhibit less average bitterness than a control solution consisting of tranexamic acid and water. In some embodiments, aqueous tranexamic acid compositions are provided comprising no less than 40% water by volume, a thickener and a surfactant that exhibit less average bitterness than a control solution consisting of tranexamic acid in water and score at least 1.0 average points higher, or at least 1.5 average points higher on a 5 point bitterness scale wherein 1 is most bitter and 5 is least bitter. The compositions may also include one or more of a sweetener, pH adjuster, viscosity enhancer, preservative and a flavoring agent. Average bitterness of a tranexamic acid oral rinse test solution may be determined in a taste test performed by at least 4 taste testers and compared to a control solution consisting of tranexamic acid and water, wherein the tranexamic acid is at the same concentration in the test and control solutions, and each solution is scored on a numeric scale of 1 to 5, wherein 1 is the most bitter and 5 is the least bitter, for example, as performed in Example 1B. The taste test is performed wherein the solutions are at about the same temperature, or at about ambient room temperature about 20 to 25° C. The solution is held in the mouth for a period of at least 10 seconds during taste testing.

Flavoring Agent

In some embodiments, an aqueous formulation of tranexamic acid is provided that is a solution formulation comprising a flavoring agent. Flavoring agents that can be added to the composition of the invention are those known in the pharmaceutical art. Typically, the flavoring agent is selected from synthetic flavor oils and/or naturally derived oils from plants, flowers, leaves, other natural flavors, natural fruit flavors, artificial flavors, artificial fruit flavors, or combinations thereof. Naturally derived oils, other natural flavors, synthetic flavors or combinations thereof include, but are not limited to, peppermint, spearmint, menthol, cinnamon, vanilla, artificial vanilla, chocolate or artificial chocolate. Natural fruit flavors, artificial fruit flavors or combination thereof include, but are not limited to, cherry, grape, orange, strawberry or lemon. In some embodiments, the flavoring agent does not contain an aldehyde moiety. In one embodiment, the flavoring agent is menthol. In one embodiment, the flavoring agent does not include carvone. In some embodiments, the flavoring agent used in the composition of the invention is present in a range of about 0.01 to about 0.20%, or about 0.02 to about 0.10% wt/vol based on the composition.

Sweetener

In some embodiments, an aqueous solution formulation of tranexamic acid is provided that includes a sweetener. In some embodiments, the sweetener is an artificial or natural non-nutritive sweetener. In some embodiments, the sweetener is selected from aspartame (Methyl L-α-aspartyl-L-phenylalaninate), acesulfame potassium (Potassium 6-methyl-2,2-dioxo-2H-1,2λ$^6$,3-oxathiazin-4-olate), neotame ((3S)-3-(3,3-Dimethylbutylamino)-4-[[(2S)-1-methoxy-1-oxo-3-phenylpropan-2-yl]amino]-4-oxobutanoic acid), saccharin (2H-1λ$^6$,2-Benzothiazol-1,1,3-trione), or sucralose ((1→6)-Dichloro-(1→6)-dideoxy-β-D-fructofuranosyl-4-chloro-4-deoxy-α-D-galactopyranoside). In some embodiments, the sweetener is selected from the group consisting of xylose, ribose, glucose, mannose, galactose, fructose, dextrose, sucrose, maltose, sorbitol, xylitol, mannitol, pentaerythritol, stevioside, neohesperidin dihydrocalcone, thaumatin, glycyrrhizin, perillartine, cyclamate, and combinations thereof. In some embodiments, the sweetener is an artificial, i.e. non-sugar, sweetener. In a specific embodiment, the sweetener is sucralose. In some embodiments, the sweetener is used in the composition in a range of about 0.02 to 1 wt/vol %, or 0.1 to 0.5 wt/vol % based on the weight of the composition when an artificial sweetener is used.

Viscosity Enhancer

In some embodiments, an aqueous formulation of tranexamic acid is provided that is a solution formulation comprising a pharmaceutically acceptable viscosity enhancer. The viscosity enhancer may be selected from sorbitol, glycerin, ethylene glycol, propylene glycol, 1,3-butylene glycol, polyethylene glycol, polypropylene glycol, xylitol, maltitol, lactitol, and mixtures thereof. In a specific embodiment, the viscosity enhancer includes propylene glycol. In some embodiments, the composition does not include sorbitol. In some embodiments, the composition does not include glycerin. The viscosity enhancer in the composition of may range from about 2 to about 8 wt %, or about 3 to about 6 wt %, or about 4 to about 5 wt % of the composition.

Preservative

In some embodiments, an aqueous formulation of tranexamic acid is provided that is a solution formulation comprising a preservative. Preservatives may be selected from any pharmaceutically acceptable preservative known in the art. In some embodiments, the preservative is selected from sodium benzoate, potassium sorbate, EDTA or salts thereof, parabens (such as methyl, ethyl, propyl and butyl p-hydroxybenzoic acids esters or mixtures thereof) or mixtures thereof. In some embodiments, methyl paraben, propyl paraben, sodium benzoate, or a mixture thereof is used as a preservative. In some embodiments, the preservative is present in the aqueous tranexamic acid solution composition at from about 0.01 to about 1.0 wt % based on the weight of the composition. In a specific embodiment, a mixture of methyl paraben and propyl paraben, is employed in a combined amount of from about 0.02 to about 0.5 wt %, or about 0.02 to 0.2 wt %, based on the weight of the composition. In some embodiments, the weight ratio of propyl paraben to methyl paraben is selected from about 1:2 to about 1:20, about 1:5 to about 1:15, or about 1:9. In some embodiments, the presence of propyl paraben aids the longevity of the preservative in the solution.

Administration

In one embodiment, a method is provided for treating a patient having a bleeding disorder, or under fibrinolytic (thombolytic) agents and/or on anticoagulant therapy (e.g., warfarin) to reduce or prevent hemorrhage during and/or following a dental procedure, comprising administering an aqueous pharmaceutical composition for topical administration in the oral cavity comprising tranexamic acid, according to the disclosure.

In some embodiments, the patient may suffer from a bleeding disorder selected from hemophilia A (factor VIII deficiency), hemophilia B (factor IX deficiency), von Willebrand disease, and other factor deficiencies including factor I, II, V, VII, X, XI, XII, or XIIIdeficiency.

In some embodiments, the patient may be on a fibrinolytic (thrombolytic) agent. In some embodiments, the fibrinolytic (thrombolytic) agent is streptokinase, tissue plasminogen activator, or urokinase. In some embodiments, the fibrinolytic (thrombolytic) agent is a tissue plasminogen activator such as a human recombinant tissue plasminogen activator (rtPA, e.g., Alteplase), derivative of recombinant human tPA (e.g., Retaplase), or Tenecteplase (TNK-tPA). In some embodiments, the fibrinolytic (thrombolytic) agent is a streptokinase (SK), such as a natural streptokinase, that has been isolated and purified from streptococci bacteria, or a complex of streptokinase and plasminogen (e.g., Anistreplase). In some embodiments, the fibrinolytic (thrombolytic) agent is urokinase (UK), a urinary-type plasminogen activator (e.g, Abbokinase®). In some embodiments, the fibrinolytic agent is a New Oral Anticoagulant (NOAC) such as an oral direct thrombin inhibitor (e.g. Dabigatran) or an oral direct factor Xa inhibitor (e.g. Rivaroxaban, Apixaban, or Edoxaban).

In some embodiments, the patient may be on anticoagulant therapy. In some embodiments, the patient is on anticoagulant therapy selected from Warfarin, Heparin, low molecular weight Heparin, Heparin sodium, Heparin/Dextrose, Dalteparin, Hirudin, Lepirudin, Bivalirudin, Argatroban, Dabigatran, Rivaroxaban, Apixaban, Edoxaban, Betrixaban, Darexaban, Letaxaban, Eribaxaban, Coumarin, Acenocoumarol, Phenprocoumon, Atromentin, Phenindione, Fondaparinux, or Idraparinux.

In some embodiments, a method is provided for treatment of a patient receiving anticoagulant therapy during and following a dental procedure is provided comprising administering an oral aqueous mouth rinse solution composition comprising an effective amount of tranexamic acid, as provided herein.

In some embodiments, a method is provided for treatment of a patient having a bleeding disorder, or patients on fibrinolytic (thrombolytic) therapy and/or receiving anticoagulant therapy, during and following a dental procedure is provided comprising administering an oral aqueous mouth rinse solution composition comprising an effective amount of tranexamic acid, as provided herein.

In a specific embodiment, a method is provided for treatment of a patient in need thereof comprising administering a composition according to the disclosure topically in the oral cavity in a solution form containing 500 mg/10 ml (5 wt %) tranexamic acid. In some embodiments, the composition is administered topically in the oral cavity in the form of a solution as an oral rinse for two minutes, immediately after the dental procedure in a patient in need thereof, e.g., a patient with hemophilia, administration can be continued three or four times daily for up to eight (8) days.

A bleeding disorder is a condition that affects the way blood clots. A bleeding disorder prevents blood of a patient from clotting properly, which can result in prolonged or heavy bleeding. Bleeding disorders include hemophilia A and B that can occur when there are low levels of clotting factors in the blood of the patient. It causes heavy or unusual bleeding into the joints. Factor II, V, VII, X or XII deficiencies are bleeding disorders related to blood clotting problems or abnormal bleeding problems. Von Willebrand's disease is the most common inherited bleeding disorder. It develops when the blood of the patient lacks von Willebrand factor, which helps the blood to clot. Certain bleeding disorders, including hemophilia, can be treated by with factor replacement therapy. Involving injection of clotting actors intravenously to the patient. In some cases if the patient with a bleeding disorder lacks certain clotting factors, a frozen plasma transfusion may be employed. Fresh frozen plasma contains factors V and VIII, which help with clotting. The transfusion must be performed in a hospital.

A patient having a bleeding disorder is typically diagnosed by a complete blood count (CBC) which measures the amount of red and white cells, a platelet aggregation test, which checks how well platelets of the patient clump together, and a bleeding time test, which determines how quickly the blood clots to prevent bleeding.

In some embodiments, the composition is indicated in patients with hemophilia or another bleeding disorder for short-term use for one to twelve days, one to ten days, two to eight days, or three to seven days to reduce or prevent hemorrhage and/or to reduce the need for factor replacement therapy during and following dental procedures. The composition may be administered for a period of at least one, two, three, four, five, six, seven, eight, nine, ten, eleven or twelve days to reduce or prevent hemorrhage and/or to reduce the need for factor replacement therapy during and following dental procedures.

In some embodiments, a method is provided comprising administering an oral rinse dosage form as provided herein comprising tranexamic acid for topical administration to the mouth of a patient in need thereof during or after a dental procedure such as tooth extraction or scaling in order to reduce bleeding, facilitate the use of antifibrinolytic therapy in dental patients and/or minimize systemic exposure from administration of the injection dosage form.

In some embodiments, a method for treating a patient in need thereof comprises administering the aqueous solution composition comprising tranexamic acid according to the disclosure topically to significantly reduce bleeding following dental procedures. In some embodiments, the oral mouth rinse composition according to the present disclosure is administered topically as a mouth rinse in a swish and spit format in an amount in the range of 2 mL to 20 mL, 5 mL to 15 mL, or about 10 mL. The mouth rinse is swished and/or held in the mouth for a period of from about 30 seconds to about 4 minutes, about 1 min to about 3 min, or about 2 minutes per administration. In some embodiments, the composition is administered one, two, three, four, five, six, seven, eight, nine or ten times per day for a period of one, two, three four, five, six, seven, eight, nine or ten days following the dental procedure. In a specific embodiment, the mouth rinse is administered as an effective amount of 10 mL of a tranexamic acid 5% wt/vol solution used for two minutes, four times daily for seven days. In another specific embodiment, the mouth rinse is administered as an effective amount of 10 mL of a tranexamic acid 5% wt/vol solution used for two minutes, four times daily for five days. In one embodiment, the mouth rinse comprising tranexamic acid is administered in a swish and spit format. In another embodiment, the mouth rinse comprising tranexamic acid is administered in a swish and swallow format.

EXAMPLES

Example 1A. Formulation Development

A Tranexamic Acid (TXA) Oral Rinse 5% formulation (Formulation A) was developed as shown in Table 1A. This formula was optimized in terms of taste and preservative effectiveness using glycerin and sorbitol. However, it was found that it discolored (turned brownish) when placed on stability at 40° C./25% RH (relative humidity) within 1 month.

TABLE 1A

Composition of Formulation A

| Component | Functionality | % (w/w) |
|---|---|---|
| PURIFIED WATER USP | Diluent | 49.55 |
| GLYCERIN, USP | Viscosity enhancer | 18.02 |
| PROPYLENE GLYCOL, USP | Viscosity enhancer | 1.8 |
| SORBITOL 70%, USP | Viscosity enhancer | 18.02 |
| TRANEXAMIC ACID (TXA) | Active | 4.5045 |
| CONCENTRATED PHOSPHORIC ACID, UN 1805 (Fisher) | pH adjuster | 0.288 |
| POLOXAMER 407 (KOLLIPHOR ® P 407), 50259528 (BASF) | Surfactant | 0.36 |
| SUCRALOSE | Sweetener | 0.063 |
| PURIFIED WATER USP | Diluent | 1.8 |

TABLE 1A-continued

Composition of Formulation A

| Component | Functionality | % (w/w) |
|---|---|---|
| METHYLPARABEN, NF | Preservative | 0.081 |
| PROPYLPARABEN, NF | Preservative | 0.009 |
| SPEARMINT FLAVOR, (F-4785) Foote &Jenks | Flavoring | 0.36 |
| PURIFIED WATER USP | Diluent | QS |
| Total | | 100.0 |

To determine which components of the formulation were responsible for the discoloration, binary mixtures of TXA and each component were dissolved in phosphoric acid solution at pH 5.5 in amounts representative to their concentration in Formulation A of Table 1A. Binary mixtures are shown in Table 1B.

TABLE 1B

Binary mixtures used to test for discoloration (wt %)

| INGREDIENT | Sample #1 | Sample #2 | Sample #3 | Sample #4 | Sample #5 | Sample #6 | Sample #7 |
|---|---|---|---|---|---|---|---|
| Glycerin, USP | — | — | 20.0 | — | — | — | — |
| Propylene Glycol, USP | — | — | — | 2.0 | — | — | — |
| Sorbitol 70%, USP | — | — | — | — | 20.0 | — | — |
| Tranexamic acid | 5.0 | 5.0 | 5.0 | 5.0 | 5.0 | 5.0 | 5.0 |
| Concentrated Phosphoric acid | — | 0.28* | 0.28* | 0.28* | 0.28* | 0.28* | 0.28* |
| Poloxamer 407 (KOLLIPHOR® P 407) | — | — | — | — | — | 0.80 | — |
| Sucralose | — | — | — | — | — | — | 0.10 |
| Purified Water USP | QS | | | | | | |
| Total | 100 | 100 | 100 | 100 | 100 | 100 | 100 |

Samples of each mixture in Table 1B were placed in glass vials and stored in 60° C. oven for 2 weeks and visually inspected periodically for discoloration. The samples from Table 1B containing TXA and Sorbitol (sample 5), or TXA and Glycerin (sample 3), or TXA and Poloxamer 407 (sample 6), or TXA and spearmint flavor F-4785, turned yellow. Thus sorbitol, glycerin, poloxamer 407 and spearmint flavor were considered to be the ingredients responsible for the discoloration of formula A.

The approach to find alternatives to these components was focused on maintaining the good taste of the formula with alternatives that maintain the properties/functions that Sorbitol, Glycerin, and Poloxamer 407 exhibit in Formulation A of Table 1A. For example, Poloxamer 407 is a surfactant that helps dissolve the flavor. Sorbitol and Glycerin are considered as secondary sweeteners and viscosity enhancers in the formula that help with masking the bitter taste of TXA.

Alternative Flavoring to Spearmint Flavor F-4785

Natural extract flavors are composed of multi ingredients and may contain aldehyde components which may react with the primary amine group of the TXA resulting in discoloration. Searching for alternatives to natural extract flavors was focused on finding a flavoring agent that was aldehyde-free, single component, and preferably natural. Menthol fulfilled all these requirements. It is a single ingredient, natural essential oil that does not contain an aldehyde functional group in its structure and is widely used in consumer health and pharmaceutical preparation even though the flavor profile is less complex than a natural extract flavor like the spearmint oil. Menthol was selected for further evaluation.

Alternative Surfactants to Poloxamer 407

There are several surfactants that are commonly used in pharmaceutical preparations. To find alternatives to Poloxamer 407 which is commonly used in mouthwash preparations, the following surfactants were tested: Tween 20, Tween 80, Sucrose Stearate, and SucroseLaurate.

Binary Mixtures Study

Binary mixtures of TXA and alternative surfactants were prepared and samples were stored in a 60° C. oven to test for discoloration as described in Table 2.

TABLE 2

Binary mixtures of TXA and surfactants Tween 20, Tween 80, Sucrose Laurate, and Sucrose Stearate

| | | | Amount (g) | | | |
|---|---|---|---|---|---|---|
| INGREDIENT | Item# | Lot# | Sample #1 | Sample #2 | Sample #3 | Sample #4 |
| Tranexamic acid | 100132 | R11845 | 5.0 | 5.0 | 5.0 | 5.0 |
| Concentrated Phosphoric acid | Fisher UN 1805 | 154772 | 0.28 | 0.28 | 0.28 | 0.28 |
| Tween 20 | Fisher BP337-500 | 153083 | 0.5 | — | — | — |
| Tween 80 | Fisher BP338-501 | 151141 | — | 0.5 | N/A | — |
| Sucrose Stearate | 420615-S | S00029 | — | — | 0.5 | — |
| Sucrose Laurate | 410413-S | S00030 | — | — | — | 0.5 |
| Purified Water USP | 200091 | N/A | QS | QS | QS | QS |
| Total | | | 100 | 100 | 100 | 100 |
| Discoloration | | | No | No | Didn't dissolve | No |

N/A = not applicable 1.2 Results:

Tween 20, Tween 80 and Sucrose Laurate didn't cause discoloration when combined with TXA and were considered as alternatives to Poloxamer 407. Sucrose Stearate did not dissolve into solution and was excluded from further development. Initial testing was focused on Tween 80 because it is more commonly used in pharmaceutical preparations.

Alternatives to Glycerin and Sorbitol

Glycerin and Sorbitol were used in the initial formulation development as secondary sweeteners and to improve the mouth feel of the product by enhancing the viscosity of the preparation. They are widely used in pharmaceutical preparation and can be incorporated at very high concentrations (up to 100%). There are many non-sugar sweeteners available, but they are similar to Sorbitol, and thus excluded from consideration.

Hydrophilic polymers such as cellulose based polymers were investigated to increase viscosity in pharmaceutical preparation such as gels or pastes. Sodium carboxymethyl cellulose (Na CMC) is widely used in solid pharmaceutical and cosmetic preparations. Sodium carboxymethyl cellulose was considered as a thickening agent to replace or augment Sorbitol and Glycerin, but it has no sweetening properties.

Binary Mixtures Study

Binary mixtures of Na CMC and TXA were prepared and stored at 60° C. for 2 weeks to test for discoloration as in Table 3.

TABLE 3

Binary mixtures of TXA and CMC

| INGREDIENT | Item# | Lot# | Amount (g) |
|---|---|---|---|
| Tranexamic acid | 100132 | R11845 | 5.0 |
| Concentrated Phosphoric acid | Fisher UN 1805 | 154772 | 0.28 |
| Sodium CMC | 200206 | R09629 | 0.5 |
| Purified Water USP | 200091 | N/A | QS |
| Total | | | 100 |
| Discoloration | | | No |

Results: Sodium CMC didn't cause discoloration. So it was considered as an alternative to Glycerin and Sorbitol for further development.

Tween 80 Based Formulations

Formulation development was next focused on using Tween 80, NaCMC, and Menthol at varying concentrations as described in Table 4A.

TABLE 4A

Composition of formulations containing Tween 80, CMC and Menthol

| | % (w/v) | | |
|---|---|---|---|
| Component | Formulation B | Formulation C | Formulation D |
| PURIFIED WATER USP | 80.0 | 80.0 | 80.0 |
| PROPYLENE GLYCOL, USP | 5.0 | 5.0 | 7.0 |
| SODIUM CMC | 1.0 | 0.75 | 0.5 |
| TRANEXAMIC ACID | 5.0 | 5.0 | 5.0 |
| CONCENTRATED PHOSPHORIC ACID | 0.3 | 0.3 | 0.3 |
| SUCRALOSE | 0.3 | 0.3 | 0.3 |
| METHYLPARABEN, NF | 0.18 | 0.18 | 0.18 |
| PROPYLPARABEN, NF | 0.02 | 0.02 | 0.02 |
| TWEEN 80 | 0.5 | 0.5 | 0.75 |
| PURIFIED WATER USP | 5.0 | 5.0 | 5.0 |
| MENTHOL | 0.05 | 0.03 | 0.03 |
| PURIFIED WATER USP | QS | QS | QS |
| Total | 100 | | 1.0 L |

Observations regarding taste and formulation characteristics for formulations B, C and D are shown in Table 4B.

TABLE 4B

Observations regarding taste and formulation characteristics for formulations B, C and D

| Observations Formulation | Changes | Evaluation |
|---|---|---|
| Formulation B | Control (baseline) Formulation: Propylene glycol = 5% NaCMC = 1% Menthol = 0.05% | Viscous (High NaCMC level), Burning sensation from Menthol |
| Formulation C | Propylene glycol = 5% NaCMC = 0.75% Menthol = 0.03% | Tasted Better than Formulation B. No burning taste. Still viscous. Turned cloudy when placed at 60° C. (Menthol was separating out) within 1 day but went back into solution when cooled to Room Temperature |
| Formulation D | Propylene glycol = 7% NaCMC = 0.5% Menthol = 0.03% | Increased Tween 80 and Propylene glycol levels to prevent phase separation. Lowered CMC to reduce viscosity. Taste was good and Viscosity was acceptable Turned cloudy when placed at 60° C. (Menthol was separating out) within 1 day but went back into solution when cooled to Room Temperature |

Alternatives to Tween 80 Based Formulations

Alternatives to Tween 80 formulations were focused on using Tween 20 and Sucrose Laurate since they didn't cause discoloration when mixed with TXA and stored at 60° C. as described in Table 5A.

TABLE 5A

Composition of formulations containing Tween 20 and Sucrose Laurate

| | % (w/v) | |
|---|---|---|
| Component | Formulation E | Formulation F |
| PURIFIED WATER USP | 80.0 | 80.0 |
| PROPYLENE GLYCOL, USP | 5.0 | 5.0 |
| SODIUM CMC | 0.5 | 0.5 |

TABLE 5A-continued

Composition of formulations containing
Tween 20 and Sucrose Laurate

| | % (w/v) | |
|---|---|---|
| Component | Formulation E | Formulation F |
| TRANEXAMIC ACID | 5.0 | 5.0 |
| CONCENTRATED PHOSPHORIC ACID | 0.37 | 0.37 |
| SUCRALOSE | 0.3 | 0.3 |
| METHYLPARABEN, NF | 0.18 | 0.18 |
| PROPYLPARABEN, NF | 0.02 | 0.02 |
| TWEEN 20 | — | 0.5 |
| SUCROSE LAURATE | 0.5 | — |
| PURIFIED WATER USP | 5.0 | 5.0 |
| MENTHOL | 0.03 | 0.03 |
| PURIFIED WATER USP | QS | QS |
| Total | 100 | 100 |

Observations regarding taste and formulation characteristics for formulations E and F are shown in Table 5B.

TABLE 5B

Observations regarding taste and formulation characteristics for formulations E and F

| Formulation | Changes | Evaluation |
|---|---|---|
| Formulation E | Sucrose Laurate = 0.5% Propylene glycol = 5% NaCMC = 0.5% Menthol = 0.03% | Tasted good. Turned cloudy when placed at 60° C. (Menthol was separating out) within 1 day and didn't go back in solution when cooled to Room Temperature. Was eliminated from further development |
| Formulation F | Tween 20 = 0.5% Propylene glycol = 5% NaCMC = 0.5% Menthol = 0.03% | Tasted good. Turned cloudy when placed at 60° C. (Menthol was separating out) after 2 weeks but back in solution when cooled to Room Temperature |

Results: Formulation F tasted good but turned cloudy after 2 weeks at 60° C. The sample went back into solution quickly when cooled down to room temperature. This formulation was considered promising and was used for further development in attempts to prevent phase separation at 60° C. by increasing the concentration of Tween 20 from 0.5% to 0.75% and 1.0%. Additionally, Na CMC level was tested at 0.5% and at 0.25% to test its impact on taste and viscosity. Formulations are shown in Table 6.

TABLE 6

Composition of formulations containing
Tween 20 and Sucrose Laurate

| | % (w/v) | |
|---|---|---|
| Component | Formulation G | Formulation H |
| PURIFIED WATER USP | 80.0 | 80.0 |
| PROPYLENE GLYCOL, USP | 5.0 | 5.0 |
| SODIUM CARBOXYMETHYLCELLULOSE | 0.5 | 0.25 |
| TRANEXAMIC ACID | 5.0 | 5.0 |
| CONCENTRATED PHOSPHORIC ACID | 0.37 | 0.34 |
| SUCRALOSE | 0.3 | 0.3 |
| METHYLPARABEN, NF | 0.18 | 0.18 |
| PROPYLPARABEN, NF | 0.02 | 0.02 |
| TWEEN 20 | 1.0 | 0.75 |
| PURIFIED WATER USP | 5.0 | 5.0 |
| MENTHOL | 0.03 | 0.03 |
| PURIFIED WATER USP | QS | QS |
| Total | 100 | 100 |

Results: Formulas with Tween 20 concentration at 0.75% and 1.0% prevented phase separation of Menthol at 60° C. Additionally lowering Na CMC level from 0.5 to 0.25% provided enough viscosity and maintained a good taste similar to formula F [[RD059-67(66?)]]. Formulations G and H were used for further development.

Refining sodium carboxymethyl cellulose levels and Taste Testing of formulations

Example 1B. Taste Testing

A study was performed to determine the amount of sodium carboxymethyl cellulose by preparing and testing new formulations containing of 0.5, 0.25, 0.1 and 0% Na CMC for palatability scoring for taste and viscosity.

Four (4) test formulations of Tranexamic acid (TXA) 5% wt/vol oral rinse were prepared as shown in Table 7 using Tween 20 surfactant with varying amounts of Sodium carboxymethyl cellulose (Na CMC) of 0.5, 0.25, 0.1 and 0%. The formulations were ranked in terms of taste and favorability in comparison to a control formulation containing TXA 5% wt/vol solution in water.

Four formulations with varying amounts of Na CMC were prepared for taste testing as described in Table 7.

TABLE 7

TXA 5 wt % Formulations for taste testing

| Component | Formulation I wt % | Formulation J wt % | Formulation K wt % | Formulation L wt % |
|---|---|---|---|---|
| PURIFIED WATER USP | 78.43 | 78.43 | 78.43 | 78.43 |
| PROPYLENE GLYCOL, USP | 4.90 | 4.90 | 4.90 | 4.90 |
| SODIUM CMC | 0.49 | 0.245 | 0.098 | 0.0 |
| TRANEXAMIC ACID, FISHER UN1805 | 4.90 | 4.90 | 4.90 | 4.90 |
| CONCENTRATED PHOSPHORIC ACID | 0.363 | 0.33 | 0.33 | 0.33 |
| SUCRALOSE | 0.29 | 0.294 | 0.294 | 0.294 |
| METHYLPARABEN, NF | 0.18 | 0.176 | 0.176 | 0.176 |
| PROPYLPARABEN, NF | 0.020 | 0.020 | 0.020 | 0.020 |
| TWEEN 20, FISHER BP337-500 | 0.98 | 0.735 | 0.735 | 0.735 |
| PURIFIED WATER USP | 4.90 | 4.90 | 4.90 | 4.90 |
| MENTHOL, USP | 0.029 | 0.029 | 0.029 | 0.029 |
| PURIFIED WATER USP | QS | QS | QS | QS |
| Total | 100.0 | 100.0 | 100.0 | 100.0 |

The taste testing was based on a swish and spit procedure. Each subject took approximately 3-5 mL of each formulation and swished the product in his/her mouth for at least 10 seconds and spit the product into a waste container. The subject rinsed his/her mouth with water to remove any residual amount of the product after each test. In addition to the four test formulations, a control formulation was employed consisting of 5% wt/vol TXA in water.

A panel of 8 tasters scored each of the four test formulations and the control formulation. Each formula was evaluated for palatability score on a favorability scale from 1 (least favorable) to 5 (most favorable) for each of the following properties:
1. Level of sweetness
2. Level of flavor
3. Level of bitterness/after taste
4. Overall likability At the end of test the formulas were ranked in terms of average palatability score by combining the individual scores of each formula. Taste test results are shown in Tables 8A to 8F.

TABLE 8A

Taste Test-Control TXA Water Solution

| Control TXA water | Level of sweetness | Level of flavor | Bitterness/ aftertaste | Overall likability |
|---|---|---|---|---|
| K1 | 1 | 1 | 1 | 1 |
| K2 | 1 | 2 | 1 | 1 |
| K3 | 3 | 2 | 3 | 4 |
| K4 | 1 | 1 | 3 | 2 |
| MB | 1 | 1 | 1 | 1 |
| MA | 1 | 1 | 1 | 1 |
| ED | 1 | 1 | 1 | 1 |
| LSY | 1 | 1 | 1 | 1 |
| avg | 1.25 | 1.25 | 1.5 | 1.5 |
| Std Dev | 0.71 | 0.46 | 0.93 | 1.07 |

TABLE 8B

Taste Test-Formulation I

| Form I | Level of sweetness | Level of flavor | Bitterness/ aftertaste | Overall likability |
|---|---|---|---|---|
| K1 | 3 | 4 | 5 | 4 |
| K2 | 3 | 3 | 2 | 3 |
| K3 | 4 | 2 | 1 | 1 |
| K4 | 2 | 3 | 4 | 3 |
| MB | 2 | 3 | 3 | 3 |
| MA | 5 | 4 | 2 | 2 |
| LSY | 4 | 1 | 2 | 2 |
| Avg | 3.29 | 2.86 | 2.71 | 2.57 |
| Std Dev | 1.11 | 1.07 | 1.38 | 0.98 |

TABLE 8C

Taste Test-Formulation J

| Form J | Level of sweetness | Level of flavor | Bitterness/ aftertaste | Overall likability |
|---|---|---|---|---|
| K1 | 2 | 4 | 4 | 3 |
| K2 | 2 | 3 | 3 | 3 |
| K3 | 2 | 2 | 3 | 3 |
| K4 | 3 | 4 | 4 | 4 |
| MB | 3 | 4 | 4 | 3 |
| MA | 4 | 3 | 3 | 3 |
| LSY | 3 | 2 | 3 | 3 |
| ED | 2 | 2 | 4 | 3 |
| Avg | 2.63 | 3.00 | 3.50 | 3.13 |
| Std Dev | 0.74 | 0.93 | 0.53 | 0.35 |

TABLE 8D

Taste Test-Formulation K

| Form K | Level of sweetness | Level of flavor | Bitterness/ aftertaste | Overall likability |
|---|---|---|---|---|
| K1 | 1 | 1 | 2 | 2 |
| K2 | 2 | 3 | 3 | 3 |
| K3 | 2 | 2 | 3 | 2 |
| K4 | 3 | 2 | 3 | 3 |
| MB | 2 | 3 | 2 | 2 |
| MA | 5 | 4 | 4 | 4 |
| LSY | 4 | 4 | 5 | 5 |
| ED | 2 | 3 | 3 | 3 |

TABLE 8D-continued

Taste Test-Formulation K

| Form K | Level of sweetness | Level of flavor | Bitterness/ aftertaste | Overall likability |
|---|---|---|---|---|
| Avg | 2.63 | 2.75 | 3.13 | 3.00 |
| STDEV | 1.30 | 1.04 | 0.99 | 1.07 |

TABLE 8E

Taste Test-Formulation L

| Form L | Level of sweetness | Level of flavor | Bitterness/ aftertaste | Overall likability |
|---|---|---|---|---|
| K1 | 1 | 1 | 2 | 1 |
| K2 | 1 | 1 | 2 | 2 |
| K3 | 2 | 1 | 2 | 1 |
| K4 | 3 | 3 | 3 | 3 |
| MB | 2 | 2 | 2 | 2 |
| MA | 5 | 3 | 4 | 4 |
| LSY | 3 | 3 | 4 | 4 |
| ED | 2 | 2 | 3 | 3 |
| AVG | 2.38 | 2.00 | 2.75 | 2.50 |
| STDEV | 1.30 | 0.93 | 0.89 | 1.20 |

The test formulations were each substantially less bitter that the control formulation containing tranexamic acid and water. Specifically, each of Formulations I, J, K, and L comprising 5% wt/vol tranexamic acid exhibited average bitterness score of 2.71(±1.38), 3.50(±0.53), 3.13(±0.99), and 2.75 (±10.89), respectively, whereas the control containing tranexamic acid 5 wt/vol % in water exhibited average bitterness scale of 1.50 (±0.93), according to the 5 point relative bitterness scale provided herein. In some embodiments, aqueous tranexamic acid compositions are provided comprising no less than 40% water by volume, a thickener and a surfactant that exhibit less average bitterness than a control solution consisting of tranexamic acid in water and score at least 1.0 average points higher, or at least 1.5 average points higher on a 5 point bitterness scale wherein 1 is most bitter and 5 is least bitter.

The individual scores for sweetness, flavor, bitterness/aftertaste and overall likability were added and averaged to arrive at overall results of the taste test which are shown in Table 8F. The formula with highest overall score was selected as the lead formula.

TABLE 8F

Overall Taste Testing Results

| Subject # | Control (5% wt/vol TXA water solution) | Formulation I | Formulation J | Formulation K | Formulation L |
|---|---|---|---|---|---|
| K1 | 4 | 16 | 13 | 6 | 5 |
| K2 | 5 | 11 | 11 | 11 | 6 |
| K3 | 12 | 8 | 10 | 9 | 6 |
| K4 | 7 | 12 | 15 | 11 | 12 |
| MB | 4 | 11 | 14 | 9 | 8 |
| ED | 4 | 15 | 11 | 11 | 10 |
| MA | 4 | 13 | 13 | 17 | 16 |
| LSY | 4 | 9 | 11 | 18 | 14 |
| AVG | 5.5 | 11.9 | 12.3 | 11.5 | 9.6 |
| STDEV | 2.8 | 2.7 | 1.8 | 4.1 | 4.1 |
| # of highest score | 1 | 3 | 3 | 3 | 0 |

Formulations I, J, K and L exhibited average palatability scores of 11.9 (±2.7), 12.3 (±1.8), 11.5 (±4.1), and 9.6 (±4.1), respectively. In contrast, control formulation consisting of 5% wt/vol TXA in water exhibited average palatability score of 5.5 (±2.8). Formulation J that contains Tween 20 at ~0.75% (w/v) and Sodium CMC 0.25% (w/v) received the highest overall average score for palatability based on sweetness, flavor, level of bitterness/aftertaste, and overall likability, as well as the lowest variability. Formulations I and J were selected for stability studies.

Example 2A. Stability Studies

Batches of Formulations I and J were prepared according to Table 8G and subjected to stability studies.

TABLE 8G

Formulations I and J for Stability Studies

| | Formulation I | | Formulation J | |
|---|---|---|---|---|
| Component | % w/w | Theoretical Quantity (g) | % w/w | Theoretical Quantity (g) |
| Purified Water USP | 78.43 | 800.0 | 78.43 | 800.0 |
| Propylene Glycol, USP | 4.90 | 50.0 | 4.90 | 50.0 |
| Sodium Carboxymethylcellulose | 0.49 | 5.0 | 0.25 | 2.5 |

TABLE 8G-continued

Formulations I and J for Stability Studies

| | Formulation I | | Formulation J | |
|---|---|---|---|---|
| Component | % w/w | Theoretical Quantity (g) | % w/w | Theoretical Quantity (g) |
| Tranexamic acid | 4.90 | 50.0 | 4.90 | 50.0 |
| Concentrated Phosphoric acid | 0.36 | 3.7 | 0.33 | 3.4 |
| Sucralose | 0.29 | 3.0 | 0.29 | 3.0 |
| Methylparaben, NF | 0.18 | 1.8 | 0.18 | 1.8 |
| Propylparaben, NF | 0.02 | 0.2 | 0.02 | 0.2 |
| Tween 20 | 0.98 | 10.0 | 0.74 | 7.5 |
| Purified Water USP | 4.90 | 50.0 | 4.90 | 50.0 |
| Menthol, USP | 0.029 | 0.3 | 0.029 | 0.3 |
| Purified Water USP | QS | QS | QS | QS |
| Total | 100 | 1020.0 g | 100 | 1020.0 g |

Formulations I and J were stored in HDPE bottles at 25° C. at 40% relative humidity (RH), and at 40° C./25% RH, as well as freeze/thaw conditions. Samples were assayed by Liquid chromatography was performed at baseline, and at each time point for tranexamic acid, propyl paraben and methyl paraben. pH of the formulations was monitored at each time point. Discoloration was also monitored.

Stability data under accelerated stability conditions when stored at 40° C./25% RH conditions is shown in Tables 9 and 10 below for Formulations I and J, respectively.

TABLE 9

12 Month Stability data: Formulation I at 40° C./25% RH HDPE bottles

| Sample description | TXA assay (% LC) | Pr. Pamben (% LC) | Me. Paraben (% LC) | Degradants (% LC) | Color | | | | pH |
|---|---|---|---|---|---|---|---|---|---|
| | | | | | l* | a* | b* | ΔF | |
| Initial | 101.1 | 99.9 | 98.6 | <RPT | 99.77 | −0.24 | 1.19 | n/a | 5.5 |
| 1 Month | 100.5 | 98.0 | 94.6 | UU0325 = 0.53 Total = 0.53 | 99.68 | −0.42 | 2.07 | 0.90 | 5.5 |
| 2 Months | 100.2 | 95.4 | 97.8 | UU0325 = 1.1 UU0434 = 0.2 Total = 1.3 | 99.7 | −0.49 | 2.41 | 1.25 | 5.5 |
| 3 Months | 101.1 | 96.5 | 94.6 | <RPT [1] | 99.51 | −0.67 | 3.09 | 1.97 | 5.5 |
| 6 Months | 100.7 | 98.9 | 98.8 | RC-C <RPT RC-D <RPT UU0324 = 0.08 Total = 0.08 | 99.39 | −0.82 | 4.09 | 2.98 | 5.5 |
| 12 Months | | | | | | | | | |
| Freeze-Thaw | 101.7 | 98.5 | 95.2 | UU0325 = 0 1 Total = 0.1 | 99.94 | −0.26 | 1.33 | 0.22 | 5.5 |

[1] Previously reported Degradant at UU0325 was found to be related to placebo so it was dropped from calculation and no longer tracked after 2 month data point. "UU" refers to Unspecified Unidentified. "<RPT" refers to below reporting threshold.

TABLE 10

12 Month Stability data: Formulation J at 40° C./25% RH HDPE bottles

| Sample description | TXA assay (% LC) | Pr. Paraben (% LC) | Me. Paraben (% LC) | [1]Degradants (% LC) | Color | | | | pH |
|---|---|---|---|---|---|---|---|---|---|
| | | | | | l* | a* | b* | ΔE | |
| Initial | 100.6 | 98.5 | 98.1 | <RPT | 99.86 | −0.19 | 0.81 | n/a | |
| 1 Month | 100.3 | 96.55 | 94.05 | UU0325 = 0.59 Total = 0.59 | 99.81 | −0.17 | 1.14 | 0.33 | 5.5 |
| 2 Months | 100.5 | 95.65 | 96.95 | UU0325 = 1.2 UU0434 = 0.2 Total = 1.4 | 99.81 | −0.23 | 1.43 | 0.62 | 5.5 |
| 3 Months | 100.6 | 95.3 | 94.35 | <RPT [1] RC-C < RPT RC-D < RPT | 99.63 | −0.38 | 1.99 | 0.82 | 5.5 |
| 6 Months | 100.4 | 97.2 | 98.3 | UU0324 = 0.09 Total = 0.09 | 99.63 | −0.47 | 2.57 | 1.79 | 5.5 |

TABLE 10-continued

12 Month Stability data: Formulation J at 40° C./25% RH HDPE bottles

| Sample description | TXA assay (% LC) | Pr. Paraben (% LC) | Me. Paraben (% LC) | [1]Degradants (% LC) | Color | | | | pH |
|---|---|---|---|---|---|---|---|---|---|
| | | | | | 1* | a* | b* | ΔE | |
| 12 Months | | | | | | | | | |
| Freeze-Thaw | 100.3 | 96.2 | 94 | UU0325 = 0.12 Total = 0.1.2 | 99.84 | −0.07 | 0.75 | 0.14 | 5.5 |

[1]Previously reported Degradant at UU0325 was found to be related to placebo so it was dropped from calculation after 2 month time point. "UU" refers to Unspecified Unidentified. . "<RPT" refers to below reporting threshold.

Results: The compositions of both Formulation I and Formulation J were capable of maintaining at least about 99.0%, 99.5%, or 99.9% of the release, or "as manufactured," amount of tranexamic acid in undegraded form after storage for 6 months at 40° C. at 25% relative humidity, as shown in Tables 9 and 10.

The compositions of both Formulation I and Formulation J were capable of maintaining at least about 95% of the release, or "as manufactured," amount of propyl paraben in undegraded form after storage for 6 months at 40° C. at 25% relative humidity.

The compositions of both Formulation I and Formulation J were capable of maintaining at least about 93% of the release, or "as manufactured," amount of methyl paraben in undegraded form after storage for 6 months at 40° C. at 25% relative humidity.

The composition of Formulations I and J did not exhibit significant discoloration after storage for 6 months at 40° C. at 25% relative humidity and exhibited ΔE*<5.

The compositions of both Formulation I and Formulation J were capable of maintaining pH 5.5 after storage for 6 months at 40° C. at 25% relative humidity.

Stability data for first six months for the 25° C./40% RH conditions is shown in Tables 11 and 12 below for Formulations I and J, respectively.

TABLE 11

12 Month Stability data: Formulation I 25° C./40% RH HDPE bottles

| Sample description | TXA assay (% LC) | Pr. Paraben (% LC) | Me. Paraben (% LC) | Degradants (% LC) | Color | | | | pH |
|---|---|---|---|---|---|---|---|---|---|
| | | | | | 1* | a* | b* | ΔE | |
| Initial | 101.1 | 99.9 | 98.6 | <RPT [1] | 99.77 | −0.24 | 1.19 | n/a | 5.5 |
| 3 Months | 100.6 | 96.7 | 94.2 | <RPT RC-C <RPT | 99.61 | −0.42 | 2.01 | 0.85 | 5.5 |
| 6 Months | 100.6 | 100.5 | 100.4 | RC-D <RPT Total <RPT | 99.71 | −0.39 | 1.93 | 0.8 | 5.5 |
| 12 Months | | | | | | | | | |
| Freeze-Thaw | 101.7 | 98.5 | 95.2 | <RPT | 99.94 | −0.26 | 1.33 | 0.2 | 5.5 |

[1] "<RPT" refers to below reporting threshold.

TABLE 12

12 Month Stability data: Formulation J at 25° C./40% RH HDPE bottles

| Sample description | TXA assay (% LC) | Pr. Paraben (% LC) | Me. Paraben (% LC) | [1]Degradants (% LC) | Color | | | | pH |
|---|---|---|---|---|---|---|---|---|---|
| | | | | | 1* | a* | b* | ΔE | |
| Initial | 100.6 | 98.5 | 98.1 | <RPT [1] | 99.86 | −0.19 | 0.81 | n/a | 5.5 |
| 3 Months | 100.4 | 95.1 | 93.6 | <RPT RC-C <RPT | 99.63 | −0.38 | 1.99 | 0.82 | 5.5 |
| 6 Months | 100.6 | 99.1 | 100.1 | RC-D <RPT Total <RPT | 99.79 | −0.17 | 1.16 | 0.4 | 5.5 |
| 12 Months | | | | | | | | | |
| Freeze-Thaw | 100.3 | 96.2 | 94 | <RPT | 99.84 | −0.07 | 0.75 | 0.1 | 5.5 |

[1]"<RPT" refers to below reporting threshold.

Results: The compositions of both Formulation I and Formulation J were capable of maintaining at least about 99.0%, or at least about 99.5% of the release, or "as manufactured," amount of tranexamic acid in undegraded form after storage for 6 months at 25° C. and 40% relative humidity, as shown in Tables 11 and 12.

The compositions of both Formulation I and Formulation J were capable of maintaining at least about 95% of the release, or "as manufactured," amount of propyl paraben in undegraded form after storage for 6 months at 25° C. at 40% relative humidity.

The compositions of both Formulation I and Formulation J were capable of maintaining at least about 93% of the release, or "as manufactured," amount of methyl paraben in undegraded form after storage for 6 months at 25° C. at 40% relative humidity.

The compositions of both Formulation I and Formulation J did not exhibit significant discoloration after storage for 6 months at 25° C. at 40% relative humidity and exhibited $\Delta E^* < 5$.

The compositions of both Formulation I and Formulation J were capable of maintaining pH 5.5 after storage for 6 months at 25° C. at 40% relative humidity.

Example 2B. HPLC Methods for Quantitation of the Active, Preservatives and Degradants in Tranexamic Acid Oral Rinse, 5% w/v The following HPLC method was employed for analysis of Tranexamic acid oral rinse formulations. Target analytes include active pharmaceutical ingredient tranexamic acid (TXA), preservative methylparaben (MPB), and preservative propylparaben (PPB). Drug product labeled amounts for tranexamic acid (TXA) were 5% w/v or 50 mg/mL; methylparaben (MPB) 1.8 mg/mL; and propylparaben (PPB) 0.2 mg/mL.

An HPLC with UV detector was fitted with C16 reverse phase column (Dionex Acclaim Polar Advantage (PA) C16, 5 um, 4.6×250 mm). Flow rate was 1.0 mL/min at 25° C. column temperature. An injection volume of 15 uL was employed. Eluate was monitored at 220 nm.

Mobile phase A was prepared by dissolving 1.2 g basic ammonium phosphate and 3.66 g of sodium perchlorate in 1000 mL deionized water (18 megaohm water). Mobile phase B was acetonitrile. HPLC gradient elution was run according to Table 13A.

TABLE 13A

HPLC Gradient Profile

| Time (minutes) | % Mobile Phase A | % Mobile Phase B |
|---|---|---|
| 0.00 | 97 | 3 |
| 7.00 | 97 | 3 |
| 35.00 | 40 | 60 |
| 36.00 | 97 | 3 |
| 42.00 | 98 | 3 |

Stock and working standard solutions of MPB/PPB and TXA were prepared. Reporting threshold standard preparation was 0.005 mg/mL TXA.

Retention time (RT), Relative retention time (RRT) relative to TXA, and Relative response factors (RRF) for TXA, MPB, PPB and related compounds A, B, C, and D are shown in Table 13B.

TABLE 13B

HPLC Retention Times, Relative Retentions times compared to TXA, and Response Factors for analytes

| Analyte | RT (min) | RRT (Relative to TXA) | RRF |
|---|---|---|---|
| TXA | 7.07 | 1.00 | NA |
| USP Related Compound C (RC C) | 7.84 | 1.11 | 0.006 |
| USP Related Compound B (RC B) | 8.89 | 1.26 | 0.84 |
| USP Related Compound D (RC D) | 9.62 | 1.36 | 0.006 |
| USP Related Compound A (RC A) | 20.78 | 2.94 | 1.23 |
| MPB | 25.68 | 3.63 | NA |
| PPB | 32.71 | 4.63 | NA |

The chemical structures of tranexamic acid and degradant compounds A, B, C and D are shown in FIG. 1.

Tranexamic acid related compound A: trans-trans-4,4'-Iminodimethylenedi(cyclohexanecarboxylic acid) is also known as "tranexamic acid dimer"

Tranexamic acid related compound B: cis-4-(aminomethyl)cyclohexanecarboxylic acid is also known as "cis-tranexamic acid".

Tranexamic acid related compound C: ((RS)-4-aminomethyl)cyclohex-1-enecarboxylic acid is also known as "1,2-didehydro tranexamic acid".

Tranexamic acid related compound D is 4-Aminomethylbenzoic acid. Systems suitability is maintained when performing sample analysis.

The amount of each of TXA, MPB, PPB in the sample compared to standards is calculated and reported to one decimal place. The amount of TXA degradants in the sample compared to standards is calculated and reported to one decimal place.

Example 2C. Method for Determination of Color (CLR) in Drug Product, Tranexamic Acid Oral Solution (TXA OS), 5% w/v A key factor in maintaining the quality of a pharmaceutical product is the color of the drug product in its final form. A colorimetric assay is used to determine the consistency of the color of drug product from batch to batch as well as throughout it shelf life by measuring changes in the product's color over time.

In this test method, the color analysis of the drug product is determined from at least one randomly chosen sample. A Colorimetric Spectrophotometer (e.g., HunterLab or equivalent may be employed. The instrument software (e.g. EasyMatchQC® software) is configured to read using the desired color scale, illuminant, and observer. The transmission cell holder is installed and the instrument is standardized as described in User's Manual. The TTRAN mode or TTRAN mode and large area view (LAV) port plate and lens position is used.

Sample is added to fill sample cell and centered over transmission port. A single color reading of the sample is taken, sample is removed, then replaced into compartment and color is read once more. The multiple color readings for a single color measurement are averaged. The average CLR values are recorded using color scale L*, a*, b* as a full color descriptor. The CLR average L, a, b values are reported.

The Color is represented by the L*a*b* value where L* represents the lightness or darkness of the sample; a* represents the redness or greenness of the sample; and, b* represents the yellowness or blueness of the sample; ΔE* (delta E*) indicates the degree of color difference and can be expressed as the root sum square of the differences in L*, in a*, and in b* from the initial L*, a*, and b* values (or the Euclidean distance).

Deltas for L* (ΔL*), a* (Δa*) and b* (Δb*) may be positive (+) or negative (−). The total difference Delta E (ΔE*), however, is always positive.

ΔL* (L*sample minus L* standard)=difference in lightness and darkness (+=lighter, −=darker);

Δa* (a* sample minus a* standard)=difference in red and green (+=redder, −=greener);

Δb* (b* sample minus b* standard)=difference in yellow and blue (+=yellower, −=bluer); and ΔE*=total color difference.

To determine the total color difference in a colorimetric assay between all three coordinates, the following formula may be used:

$$\Delta E^* = [\Delta L^{*2} + \Delta a^{*2} + \Delta b^{*2}]^{1/2}.$$

A delta E* (ΔE*) value of about 2.35 is defined as a color result that is a Just Noticeable Difference (JND); with values less than (<) no change is observable (not significant). The value of 2.35 is perceived as the value at which the human eye can start detecting differences in color. In some embodiments, tranexamic acid formulations are provided that exhibit minimal discoloration as determined by ΔE*<3, <4, or <5 after storage for at least 6 months at about 25° C. and about 40% relative humidity in a colorimetric assay.

A ΔE* value specification threshold in the range of <4, <5, <6, <7, <8, <9 or <10 may be employed to determine sample stability over time.

In a particular aspect, stable tranexamic acid compositions are provided, exhibiting a ΔE* value of <5 when stored at 25° C. at 40% RH after a period of 3 months, 6 months, 9 months, or 12 months. In another particular aspect, stable tranexamic acid compositions are provided, exhibiting a ΔE* value of <5 when stored at 40° C. at 25% RH after a period of 3 months, 6 months, 9 months, or 12 months.

Clinical Studies

The following clinical studies will be performed to demonstrate the safety and efficacy of Tranexamic Acid Mouth Rinse solution in preventing bleeding in hemophilia patients following dental scaling procedure. The intended indication of the Tranexamic acid oral rinse solution is to treat patients with hemophilia for short-term use (two to eight days) to prevent or reduce hemorrhage, and reduce the need for replacement therapy, during and following dental procedure.

Example 3. Tranexamic Acid Oral Rinse-Phase 1 Pharmacokinetic Study

An open label, randomized, two-treatment, single-dose and multiple-dose study will be performed to assess the pharmacokinetic and safety profile of Tranexamic Acid oral Rinse in maximal use and normal use conditions in healthy subjects following tooth extraction.

The pharmacokinetic study will be performed with the objective to assess the pharmacokinetic profile (Cmax, AUC0-t, AUC0-∞, Tmax, t½ and Kel) in maximal use condition (swish and swallow) and normal use condition (swish and spit). This study will be conducted in healthy subjects who are following a tooth extraction procedure to assess the effect of the oral wounds on the pharmacokinetic profile of Tranexamic acid oral rinse in plasma.

The primary objective of the study is (1) to characterize the absorption of Tranexamic Acid oral rinse after administration of a single-dose in maximal use condition (swish and swallow) and normal use condition (swish and spit), and (2) to characterize the pharmacokinetics of tranexamic acid after administration of a multiple-dose in maximal use condition (swish and swallow) in healthy subjects following a tooth extraction procedure. Time to clot formation will also be measured. The secondary objective of the study is to assess the safety and tolerability of Tranexamic acid oral rinse.

This is an open label, randomized, two-treatment, single dose study. The dose of 10 mL of 5% Tranexamic Oral Rinse (500 mg/10 mL) is selected for the study as the administration by mouth rinsing of this dose leads to a saliva tranexamic acid level range (from 2.54 to 1.27 $10^3$ mol/L) corresponding to the in-vitro fibrinolysis inhibition activity levels of this compound (from 3.00 to 1.00 $10^3$ μmol/L). This dose will also be used in the phase 3 study.

The subject will remain in the clinic at least 1 hour prior to study drug administration and until 12 hours after study drug administration.

For Arm 1 and Arm 2, blood and saliva samples will be collected from all the subjects in the study at pre-dose (0.00) and post-dose at 0.083, 0.25, 0.50, 1.00, 1.50, 2.00, 2.50, 3.00, 3.50, 4.00, 8.00, 12.00 and 24.00 hours The subject will have to come back to the clinical for the last blood sample draw, at 24 hours post-administration. For Arm 3, blood and saliva samples will be collected from all the subjects in the study at pre-dose (0.00) and post-dose at 1.00, 2.00, 3.00, 4.00, 5.00, 6.00, 7.00, 8.00, 8.50, 9.00, 9.50, 10.00, 11.00, 12.00 and 24.00 hours.

A cannulation will be carried out before the pre-dose sample collection and will be kept till the 12 hour sample collection. Later on, the cannula will be removed and sample collection will be done by direct venipuncture for the 24 hours sample collection. A medical examination will be performed at 24±2 hours post-dose.

36 healthy subjects (12 subjects per treatment arm) between 18 and 45 years of age will be enrolled in the study. Inclusion criteria for each subject include healthy, human volunteer of age between 18 and 45 years old with a Body Mass Index (BMI) between 18.50 kg/m2 and 30.00 kg/m2 (inclusive), and a body weight between 50 and 100 kg. Subjects scheduled to undergo tooth extraction (pre-molar, or molar, right or left, upper or lower).

Generally healthy as documented by the medical history, physical examination and vital sign assessments, non-smokers. If a female, must be postmenopausal (no spontaneous menses for at least 2 years), surgically sterile, abstinent, or, if sexually active, be practicing an effective method of birth control before entry and throughout the study. If a female, must have a negative pregnancy test (plasma β-hCG) at Screening and Baseline.

Exclusion criteria include Subjects with congenital or acquired conditions that predispose to bleeding (e.g. hemophilia, thrombocytopenia, coagulopathy, hematologic disease and moderate to severe hepatic impairment) are excluded.

Treatment Groups Include:

Arm 1: Tranexamic Acid oral 10 mL of 5% wt/vol (500 mg/10 mL), rinse swish and swallow (maximal use condition).

Arm 2: Tranexamic Acid oral 10 mL of 5% wt/vol (500 mg/10 mL), rinse swish and spit (normal use condition)

Arm 3: Tranexamic Acid oral 10 mL of 5% wt/vol (500 mg/10 mL), rinse swish and swallow (multiple dose maximal use condition)

For Arm 1 and Arm 2, the subject will remain in the clinical at least 1 hours prior to study drug administration and until 12 hours after study drug administration. The subject will come back to the phase 1 unit for a 24-hour post-dose visit. For Arm 3, the subject will be housed in clinic for not less than 12.00 hours prior to drug administration and till 36.00 hours after drug administration. Checkout will be done on Day 2 of the study.

Safety assessments will include Adverse events, laboratory examination, Physical examination, ECG examination, vital signs.

Pharmacokinetic Parameters will include Cmax, AUCO-t, AUCO-∞, Tmax, t½, Kel and will be estimated for plasmatic Tranexamic Acid.

Overview of Statistical Plan Non-compartmental Analysis: for each PK parameters, except Tmax, the following summary statistics will be calculated: median, maximum, minimum, arithmetic mean with 95% confidence interval, SD, coefficient of variation, geometric mean with 95% confidence interval and standard deviation of logarithmically transformed data. For Tmax, median, minimum, arithmetic mean and SD will be calculated.

Example 4. Phase 3 Efficacy Study

A well-controlled study will be performed to demonstrate the efficacy of Tranexamic Acid Mouth Rinse solution is preventing bleeding in hemophilia patients following a dental scaling planning procedure.

This study will be a randomized, double-blind, controlled study comparing the efficacy and safety of tranexamic acid as a mouth rinse to factor replacement therapy in the prevention of bleeding following dental procedure in patients with hemophilia.

The main objective of this study is to demonstrate that oral rinse solution provided herein containing tranexamic acid is at least as effective as factor replacement therapy (non-inferiority study) in the treatment and prevention of bleeding following a dental procedure (root scaling, teeth extraction and root canal) in patients with hemophilia.

The use of Tranexamic Acid Oral Rinse will reduce the need for replacement therapy. Replacement Therapy are responsible for the development of inhibitors (Gringer, 2003), which may lead to life-threatening conditions for the patients. A study from CDC (Walsh, 2015) demonstrated that patients who had developed Replacement Therapy inhibitors are at 70% higher risk of mortality compared to those without inhibitors. Therefore, Tranexamic Acid Oral Rinse may have a clinically meaningful effect on prevention of a disease with potentially serious outcome, irreversible morbidity, or even mortality.

Previous clinical studies have demonstrated that the use of local antifibrinolytic therapy with Tranexamic acid as a supplement to the currently used systemic therapy significantly reduces in the incidences of postoperative bleeding (Franchini, 2005), (Hamid, 2008), (Tavenner, 1972) and (Forbes, 1972)).

In addition, A. H. P. Lee et al. in 2005 (Lee, 2005) and Sivakumar Nuvvula et al. in 2014 (Nuvvula, 2014), demonstrated the efficacy effect of Tranexamic Acid mouthwash in controlling bleeding after dental scaling in people with hemophilia. They demonstrated that Tranexamic Acid oral rinse formulation can be used as a supplement to Factor Replacement Therapy in dental scaling procedure. A 5% Tranexamic Acid aqueous solution (500 mg/10 mL) was used in these two clinical trials.

An oral rinse solution (Tranexamic acid oral rinse) according to the disclosure will be used to treat patients with moderate and severe hemophilia for short-term use (two to eight days) to prevent or reduce hemorrhage, and reduce the need for replacement therapy, during and following dental procedure.

The primary objective is to determine the effect of Tranexamic Acid oral rinse and FRT in bleeding events from Day 0 (post-procedure) to Day 7 in all patients.

The secondary objectives are to determine the effect of Tranexamic Acid oral rinse and FRT in the immediate post-procedure bleeding severity; to determine the effect of Tranexamic Acid oral rinse and FRT (factor replacement therapy) in the use of "on-demand" FRT when bleeds occur from Day 0 (post-procedure) to Day 7 in all patients; to time bleeding post-procedure; and to assess the tolerability and safety of Tranexamic Acid oral rinse and FRT.

This is a randomized, double-blind, active-controlled study.

The dose of 10 mL of 5% Tranexamic Oral Rinse (500 mg/10 mL) is selected for the study.

The patients will be randomized in a 1:1 ratio to the experimental treatment group involving saline transfusion followed by Tranexamic Acid Oral Rinse, or the control treatment group involving FRT followed by vehicle mouthwash.

The patients will be asked to rinse their mouth with Tranexamic acid 5% aqueous solution (500 mg/10 mL) for 2-minute immediately following dental procedure (root scaling, teeth extraction and root canal) planning, and for 2-minute 4 times daily during 7 days following dental procedure. The mouthwash solution must be swilled gently for 2-3 minutes and expelled.

The patient will remain 8 days on the trial, from dental procedure (Day 0) to End-of-Study Visit (Day 7). The total duration of the treatment is 8 days.

The last visit will happen at the End-of-Study Visit (Day 7) 7-days post-procedure.

Around 108 haemophilic patients scheduling to undergo a dental procedure (54 patients per arm) will be enrolled in the study.

Treatment Groups Include

Arm 1: placebo (matching to FRT injection)+Tranexamic acid–5% Oral Rinse (500 mg/10 mL), one 2-minute oral rinse following dental procedure, and one 2-minute oral rinse 4 times daily during 7 days following dental procedure. The mouthwash solution must be swilled gently for 2-3 minutes and expelled.

Arm 2: FRT injection, pre-operatively+vehicle (matching to TXA oral rinse)

"On-demand" FRT is allowed during the course of the study (from Day 0 to Day 7) when bleeds occur (recorded by the patient in a diary card).

Efficacy assessments include for the primary objective to determine the effect of Tranexamic Acid oral rinse and FRT in bleeding time post-dental procedure.

Plasmin level in saliva and plasma before and after Tranexamic Acid Oral Rinse will be measured.

To determine the effect of Tranexamic Acid oral rinse and FRT on the immediate post-dental procedure bleeding severity, bleeding classification performed by the physician will use the following scale:

0—No bleeding
1—Light bleeding blood in saliva
2—Moderate Bleeding
3—Bleeding controlled with local measures
4—Severe Bleeding when surgical intervention is required The number of bleeding events and bleeding score will be recorded, bleeding score will be recorded by the patient in a diary card from Day 0 (post-procedure) to Day 7.

Bleeding score <1 will be considered as minor bleeding events.

The bleeding classification will be performed by the patients using the following scale:
0—No bleeding
1—Blood stained saliva
2—Bleeding that stopped after compression bandage and ice pack for 20 minutes
3—Bleeding stopped only after professional intervention

We claim:

1. An aqueous pharmaceutical solution comprising:
   about 3% wt/vol to about 7% wt/vol tranexamic acid;
   greater than 50 wt % water
   0.1% wt % to 2 wt % polyoxyethylene sorbitan monolaurate;
   0.1 wt % to 0.5 wt % sodium carboxymethyl cellulose;
   about 3 wt % to about 6 wt % propylene glycol;
   about 0.01 wt % to about 0.20 wt % menthol;
   about 0.02 wt % to about 0.5 wt % of a mixture of propyl paraben and methyl paraben; and
   a pH adjuster in an amount sufficient to adjust the pH to 4.5 to 6.5;
   wherein (a) wherein the solution does not include carvone or a flavoring agent containing an aldehyde moiety, (b) the solution retains at least about 90% of the tranexamic acid in solution in undegraded form after storage for 6 months at about 25° C. and about 40% relative humidity, and (c) the solution exhibits minimal discoloration as determined by AF* <5 after storage for 6 months at about 25° C. and about 40% relative humidity.

2. The solution of claim 1, wherein the solution exhibits an average palatability score at least 2 points higher than a control solution consisting of tranexamic acid and water.

3. The solution of claim 2, wherein the solution exhibits an average palatability score at least 3 points higher than a control solution consisting of tranexamic acid and water.

4. The solution of claim 1, wherein the solution exhibits lower average bitterness than a control solution consisting of tranexamic acid in water and scores at least 1.0 average points higher on a 5 point bitterness scale wherein 1 is most bitter and 5 is least bitter.

5. The solution of claim 1, wherein the pH adjuster is phosphoric acid.

6. An aqueous pharmaceutical solution for topical administration in the oral cavity comprising:
   about 3% wt/vol to about 7% wt/vol tranexamic acid;
   greater than 50 wt % water
   0.5 wt % to 2 1 wt % polyoxyethylene sorbitan monolaurate;
   about 0.01 0.1 wt % to about 0.5 wt % sodium carboxymethyl cellulose;
   about 3 wt % to about 6 wt % propylene glycol;
   about 0.01 wt % to about 0.2 wt % menthol;
   about 0.02 wt % to about 0.5 wt % of a mixture of propyl paraben and methyl paraben; and
   a pH adjuster in an amount sufficient to adjust the pH to 4.5 to 6.5;
   wherein (a) the solution does not include carvone or a flavoring agent containing an aldehyde moiety, (b) the solution retains at least about 90% of the tranexamic acid in solution in undegraded form after storage for 6 months at about 25° C. and about 40% relative humidity, and (c) the solution exhibits minimal discoloration as determined by AF* <5 after storage for 6 months at about 25° C. and about 40% relative humidity.

7. The solution of claim 1, where the solution comprises from about 30 mg/ml to about 70 mg/mL tranexamic acid.

8. The solution of claim 6, where the solution comprises from about 30 mg/ml to about 70 mg/mL tranexamic acid.

9. The solution of claim 6, where the pH adjuster is phosphoric acid.

10. The solution of claim 6, wherein the pH adjuster is present in an amount sufficient to adjust the pH to about 5.5.

11. The solution of claim 5, where the phosphoric acid is present in an amount sufficient to adjust the pH to about 5.5.

12. The solution of claim 9, where the phosphoric acid is present in an amount sufficient to adjust the pH to about 5.5.

* * * * *